(12) United States Patent
Bowen

(10) Patent No.: US 7,018,592 B2
(45) Date of Patent: Mar. 28, 2006

(54) METHODS AND APPARATUS FOR STERILIZING CONTAMINATED DEVICES

(76) Inventor: John G. Bowen, P.O. Box 4343, San Dimas, CA (US) 91773

( * ) Notice: Subject to any disclaimer, the term of this patent is extended or adjusted under 35 U.S.C. 154(b) by 639 days.

(21) Appl. No.: 10/180,845

(22) Filed: Jun. 26, 2002

(65) Prior Publication Data

US 2004/0001783 A1 Jan. 1, 2004

(51) Int. Cl.
*A61L 2/06* (2006.01)
(52) U.S. Cl. ............... 422/295; 422/298; 422/300; 422/26
(58) Field of Classification Search ............ 422/26, 422/28, 38, 295, 298, 300, 109, 116; 219/385
See application file for complete search history.

(56) References Cited

U.S. PATENT DOCUMENTS

| 4,376,096 A | 3/1983 | Bowen |
| 5,520,892 A | 5/1996 | Bowen |

*Primary Examiner*—John Kim
*Assistant Examiner*—Sean Conley

(74) *Attorney, Agent, or Firm*—Gale H. Thorne

(57) ABSTRACT

A self-contained, single manual step unit for thermally sterilizing dental and medical instruments is disclosed. The unit, which requires only activation of a single manual switch and which controls an autoclaving cycle by monitoring temperature of matter which changes states between solid and liquid at a predetermined temperature, provides an effective autoclaving instrument. In disclosed embodiments, each unit comprises a protective housing with a pressure containing releasible lid, a heated vessel and a cooling assembly. Thermal regulation and autoclaving timing is determined by mass and thermal characteristics of the matter and by an electrical control circuit comprised primarily of electric heaters and thermally controlled switches. Steam for autoclaving is provided by capsules or other water containers disposed within a well of the vessel at the beginning of an autoclaving cycle. Also disclosed are parts containers or transporters or which may be displaced into the well along with contents to be sterilized. Such parts containers or transporters may be sharps containers, bags and medical device wraps. The bags may be bicompartmental in form wherein one of the compartments contains water and is perforateable to deliver autoclaving steam for sterilizing items disposed in the other compartment. Parts of sharps containers may be sealed together as a result of melting of synthetic resinous material resident on the sharps container during a sterilization cycle.

30 Claims, 19 Drawing Sheets

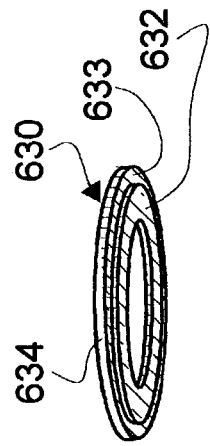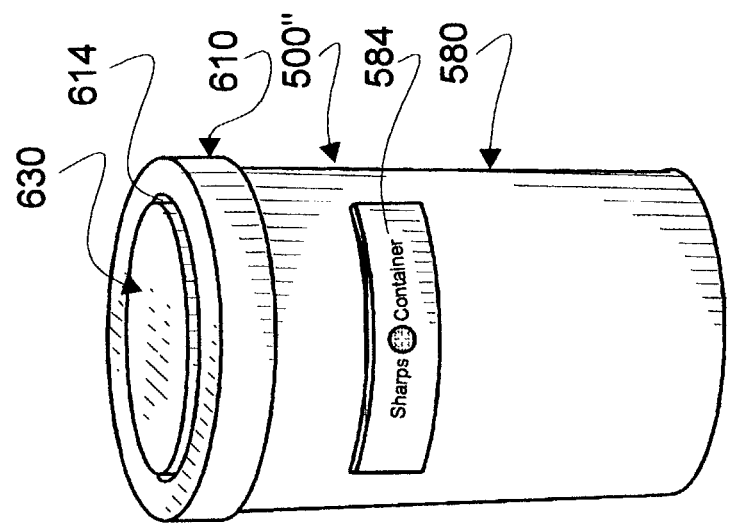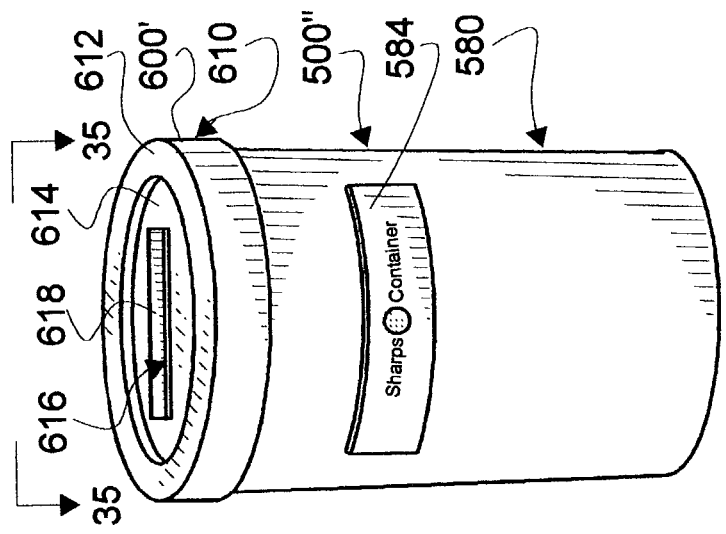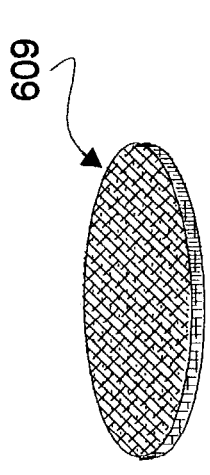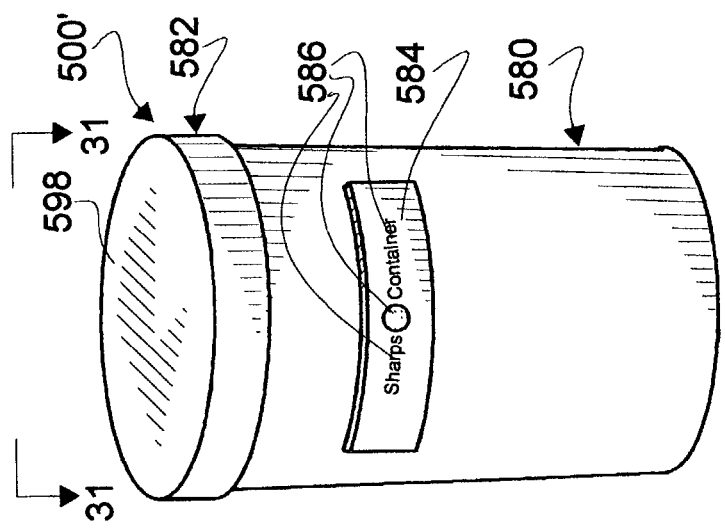

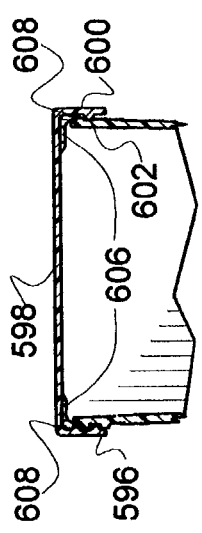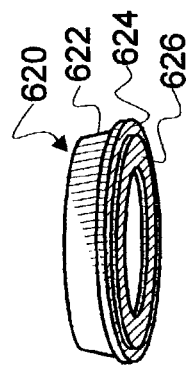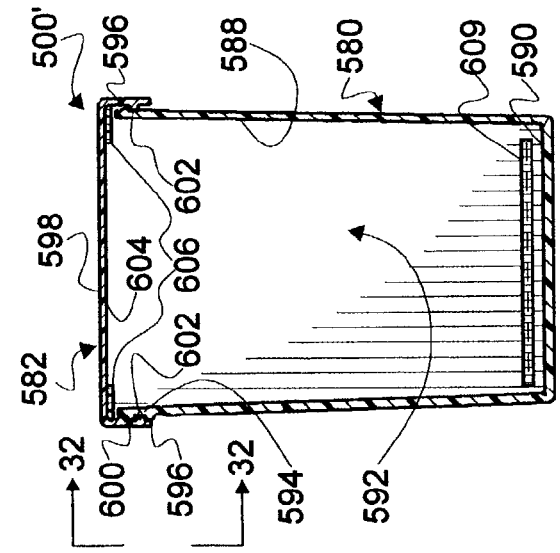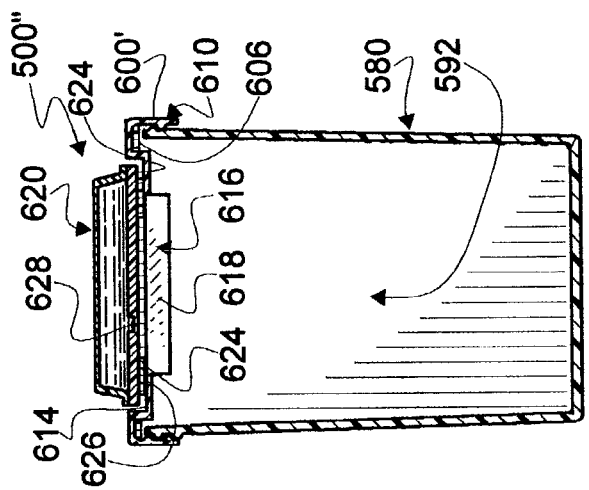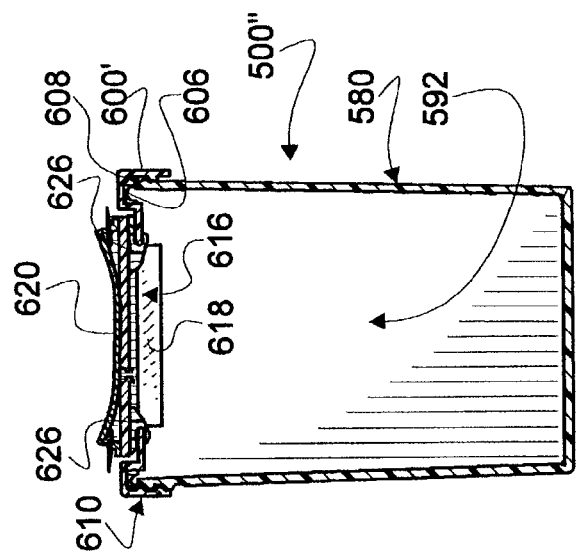
FIGURE 36
FIGURE 34
FIGURE 35
FIGURE 32
FIGURE 31

METHODS AND APPARATUS FOR STERILIZING CONTAMINATED DEVICES

FIELD OF INVENTION

This invention is concerned with methods and apparatus for sterilizing devices, especially dental and medical devices and particularly disposable medical single use devices being sterilized for reuse and for safer disposal, such as contaminated medical sharps. It is particularly concerned with sterilizing devices disposed for sterilization in plastic containers.

BACKGROUND AND RELATED ART

The invention is of the same general type as described and claimed in U.S. Pat. No. 4,376,096 ('906) and U.S. Pat. No. 5,520,892 ('892), both being issued to the same artificer of this invention. U.S. Pat. No. '906 discloses and claims a dry heating unit for disinfecting purposes which utilizes a heat conductive substance which changes state when heated to a desired temperature to aid in temperature control of the unit.

U.S. Pat. No. '892 discloses and claims a sterilization unit for dental handpieces and other instruments which combines heat, steam pressure and time in a precisely controlled manner so that the handpieces, or other surgical instruments are not damaged during sterilization. Using two manual steps, a total sterilization cycle time of less than 20 minutes is achieved. An elongated heat conductive cylindrical housing provides a container in which items are housed for sterilizing. Mineral free water is vaporized within the container to provide saturated steam flow through and about the items. A separate tubular cooling tube for receiving the container is used for transferring heat from the container.

The need for use of only sterile instruments in dentistry and medicine is widely known and universally accepted. This need has driven the medical device industry toward disposable single use devices (SUD's) across a broad spectrum of medical applications. Use of SUD's generally provides assurance of a known and acceptable level of sterility and instrument integrity. However, replacement costs of SUD's is known to place an undesirable burden on health care in a large number of medical procedures. In many cases, sterilization may reduce instrument cost considerably without a deleterious effect on a medical procedure. It has been shown that, properly performed, SUD's may be sterilized and reused with safety and efficacy. Emphasis of the correctness of this premise is found in an article entitled, "*Justify Device Reuse Curbs on Your Labels, FDA Says.*" by James G. Dickinson, published in Medical Devices & Diagnosis Industry, August 2000, beginning on page 34. As found at the bottom of page 34, ". . . the GAO study indicated that some SUDs can be safely reprocessed if appropriate cleaning, testing, and sterilization procedures are carefully followed." And further, from page 36, ". . . the proper reprocessing of some SUDs poses no threat to public health and can save hospitals up to 50% of the cost of new devices."

Also, use of SUD's has resulted in a growing medical waste disposal problem. Of special concern are problems associated with growing large volumes of insulin syringes and needles and other sharp invasive paraphernalia used by patients outside hospitals and doctors offices. In such cases, not only is initial sterilization of each product an issue, but also a significant issue is the likelihood of secondary sticks, by potentially infectious used needles and other sharp items, of those who subsequently must handle contaminated product disposal. While, in this case, sharps containers may be employed, the containers, themselves, may become incubators which substantially increase likelihood of spread of agents which are necessarily disposed with each product.

Predominantly, contemporary sterilization in hospitals and other medical and dental facilities is performed by pressure controlled autoclaves. Such autoclaves generally significantly diminish air content within the autoclave so that measured pressure better represents temperature of the autoclave. In many cases, the air is removed at the beginning or during early phases of the sterilization cycle, providing opportunity for dispensing contaminated particles outside the autoclave before being effectively decontaminated by the sterilization process in progress. Also present day heat sterilization techniques tend to damage dental handpieces and other parts having critically machined edges and surfaces due to excessive temperatures reached during autoclaving.

BRIEF SUMMARY AND OBJECTS OF THE INVENTION

In brief summary, this novel invention alleviates all of the known problems related to making and using a single manual step autoclave which is fully self-contained throughout an entire sterilization cycle. Temperature, throughout each autoclaving cycle, is precisely controlled to assure minimal damage to parts being autoclaved. As well, such temperature control provides an added benefit of permitting plastic receptacles to be as used as parts containers in the autoclave.

Generally, the presently disclosed invention involves a single-manual-operating-step autoclaving device and comprises a housing; a vessel in which items are placed for sterilizing; a lid which covers and seals the vessel; a source of water, for producing steam, contained within the vessel; and a thermal regulation assembly and electrical control system which determines composition of each sterilization cycle. Autoclaves made according to this invention are differentiated from other autoclaves by single manual step operation, thermal control of the autoclaving process and elimination of all requirements for purging of air from the autoclave. Precisely controlled temperatures which are held below melt points of a wide range of synthetic resinous materials permit plastic containers to be used as carriers for items being sterilized.

Housings made according to the invention are insulated to conserve sterilizing heat being directed into the vessel and to provide a safety barrier to ambient environment. The vessel generally provides a well which is closed at the bottom and accessible through an open top. The lid, which is affixed to the housing and opened to provide access to the well, is designed to provide a pressure seal for the vessel. As such, the seal must withstand pressures of both steam and heated air captured within the vessel at the time the lid is closed.

As is well known by Dalton's law of partial pressures. The pressure exerted by a mixture of gases is equal to the sum of the separate pressures which each gas would exert, if it alone occupied the volume of the vessel when closed. Such is expressed by:

$$PV = V(p_1, p_2, p_3, \text{etc.})$$

Where P is total pressure, V is volume of the enclosed vessel and each $p_n$ represents a partial pressure of an individual gas in the mixture. Further, for each gas(n) in the mixture the pressure/volume relationship (Charles' law or Guy-Lussac's law) is governed by:

$$P_n V = N R_n T$$

Where N represents the number of molecules of gas(n) present in the closed vessel and T represents temperature measured in absolute units (i.e. degrees Kelvin). $R_n$ represents the gas constant for gas(n). For an autoclave to be temperature controlled, the lid must be capable of providing a seal which withstands the sum of all partial pressures exerted by the individual gases in the vessel at the highest temperature reached during any portion of an autoclaving cycle. As an example, if the control temperature is chosen to be 145° Centigrade (approximately 418° Kelvin), the pressure of saturated steam is in the range of 46 pounds per square inch ($lbs/in^2$). Pressure of atmospheric gas (at an ambient pressure of 14.7 $lbs/in^2$) trapped within the closed vessel would reach an absolute pressure of about 20.5 $lbs/in^2$ at 145° Centigrade. The resulting total absolute pressure would be about 66.5 $lbs/in^2$ or a gauge pressure of 51.8 $lbs/in^2$. Lids provided for the instant invention must satisfy, with appropriate overpressure safeguards, such sealing specifications. It should be noted that reducing the control temperature likewise reduces the required sealing pressure and that lower temperatures (in the range of 121° Centigrade) have been used in autoclaves.

Fundamental to the invention is a volume of matter which is in one state prior to initiating an autoclaving cycle and which changes state (preferably from a solid to a liquid) at a predetermined rate while maintaining a substantially constant temperature until all of the material has changed state. The matter is placed in an enclosed chamber which surrounds and is in caloric communication with the vessel. In one embodiment, the chamber is designed to be a part of the vessel whereby heat is differentially communicated between the chamber and the vessel through vertical sides and the bottom of the vessel. A heat conductive material may also be disposed on the inner side of the lid (when closed) to facilitate caloric communication between the chamber and vessel.

Heat is supplied to the matter during an autoclave cycle in a manner which ultimately results in the matter totally changing state. The volume of the matter and rate of heat being transferred into the matter is controlled to provide a predetermined period for an autoclave cycle. Such a period is based upon reaching and maintaining a temperature within the vessel for a period which assures adequate sterilization. Such temperatures and periods are well known and documented in the art of autoclaving.

Also fundamental to the invention is a cooling cycle, automatically begun at the end of the sterilization cycle. Though this may be accomplished by a timing mechanism, it is preferred to begin the cooling cycle when temperature of the matter begins to sharply rise above the state-change temperature once all of the matter has liquified. Once begun, the cooling process is generally accelerated by activation of a cooling apparatus.

Sensing of conditions consistent with ending the sterilization cycle, initiating the cooling cycle and ultimately signaling a final end of each autoclave cycle is performed by the thermal regulation assembly and associated electrical control assembly. As well as basic controls exerted over heating and cooling, the electrical control assembly displays unit status, provides for manually interrupting a cooling cycle, adds increased heating when ambient temperature is below a predetermined level, sounds an alarm when vessel pressure does not exceed a desired level at a predetermined point in the sterilization cycle and terminates unit operation upon exceedingly high amperage or temperature conditions.

Saturated steam, within the vessel, is achieved through a source of water disposed within the vessel along with items to be sterilized. In some cases, the source is disposed to provide a flow of steam through predetermined orifices which are a part of a sterilizing assembly disposed within the vessel with items to be sterilized. In other cases, the source is disposed in intimate contact with the items, as for example, in a wrap, which shrouds a medical kit. Generally, the source is provided as a sealed capsule or packet of water. Though not necessary within the scope of the invention, the water used is preferably ultra-pure (i.e. having a specific conductance of less than or equal to 0.055 micromhos/centimeter).

Such capsules or packets are either breached as items are loaded into the vessel or as heat within the vessel results in increasing pressure in the capsule which causes a portion of the capsule or packet to rupture. Each capsule or packet contains sufficient liquid to assure achieving and maintaining saturated steam within the vessel throughout a sterilizing cycle.

An ink mark, which changes color to indicate having achieved a predetermined temperature for a given period of time, may be disposed on the capsule or packet to provide an indicator of effectiveness of a sterilization cycle. Such ink marks may be placed on gummed labels which may be removed from the capsule or packet and relocated to a report sheet as a record. As an added indicator, capsules and packets are made to collapse under vessel pressure to provide a further indicator of effectiveness of achieved pressure during the sterilization cycle.

Accordingly, it is a primary object to provide a single manual step autoclave for thermally sterilizing dental and medical and other contaminated items which is totally self-contained, permitting neither gas ingress into nor egress from an autoclave vessel throughout heating and cooling portions of a sterilizing cycle.

It is another primary object to provide an autoclave wherein a total heating and cooling cycle of the autoclave is determined by a rate at which matter undergoes a state of change (e.g. between solid and a liquid states).

It is still another primary object to provide a single manual step autoclave which is precisely temperature controlled by matter undergoing a state change (e.g. from solid to liquid) at a temperature which is consistent with producing saturated steam.

It is a fundamental object to provide a source of water, from which saturated steam is generated, disposed within a sealed well of the autoclave at the beginning of an autoclave cycle.

It is an object to provide a source of water which is sealed at the beginning of an autoclave heating cycle, but which ruptures due to introduction of heat into the autoclave.

It is an object to provide an ink mark associated with the source which changes color as a result of passing through a sterilizing cycle.

It is another object to provide the ink on a removable label which can be transferred to chronicle results of autoclaving.

It is another fundamental object to provide an autoclave in which plastic containers, containing parts to be sterilized, can be effectively disposed for easier and safer handling of the parts throughout a sterilization process.

It is an object to provide a plastic container (e.g. a sharps container) which forms a seal between a cover and associated container during a sterilizing cycle of an autoclave.

It is an object to provide a way of terminating action of the autoclave for access to parts being sterilized before end of the cooling cycle.

It is an object to provide an autoclave contoured to fit a container used for transporting parts to be sterilized.

It is an object to provide an automatic autoclave void of electronic timers and other electronic parts.

It is an object to provide apparatus which is automatically activated to accelerate cooling of autoclave contents following a heating (i.e. sterilization) period.

It is an object to provide indicators which are illuminated to provide evidence of operational status of the autoclave.

It is an object to provide safety features for the autoclave, such as thermal overload detectors, low pressure warning and excess amperage fusing.

These and other objects and features of the present invention will be apparent from the detailed description taken with reference to accompanying drawings.

BRIEF DESCRIPTION OF THE DRAWINGS

FIG. 29 is a perspective of a container which may be used for medical instruments, including medical sharps, and which is similar to the sharps container seen n FIG. 25.

FIG. 30 is a disk made from highly absorbent material sized and dimensioned to fit within a container, such as the container seen in FIG. 29.

FIG. 31 is a cross section made along lines 31—31 in FIG. 29.

FIG. 32 is a portion of the cross section seen in FIG. 31, taken along lines 32—32 of FIG. 31, but after sterilization in an autoclave made according to the present invention FIG. 33 is a perspective of a sharps container having a protected opening to lessen likelihood of sharps being inadvertently dispensed from the sharps container after being stored therein.

FIG. 34 is a perspective of a capsule similar to the capsules seen in FIGS. 18 and 19, but having a sealing ring of synthetic resinous material affixed to a part thereof.

FIG. 35 is a cross section of the sharps container taken along lines 35—35 of FIG. 33, with the capsule, seen in FIG. 34, disposed on the top thereof.

FIG. 36 is a cross section, similar to the cross section seen in FIG. 35, but following having been sterilize in an autoclaving cycle according to present invention.

FIG. 37 is a perspective of a stopper sized and dimensioned to fit protectively cover the opening of the container seen in FIG. 33.

FIG. 38 is a perspective of the container of FIG. 33 with the stopper seen in FIG. 37 disposed to cover hew opening of the container.

DETAILED DESCRIPTION OF THE ILLUSTRATED EMBODIMENTS

Reference is now made to the embodiments illustrated in FIGS. 1-38 wherein like numerals are used to designate like parts throughout. In some cases where parts are similar in form and function, but not identical, to numbered parts, primes of the first part numbered are used to identify the similar parts. In a like fashion, other parts having similar form and function to parts having primed numbers may be identified with the same numbers double primed.

Generally, the term "superior (or superiorly)" is used to indicate position of an item above a reference. The term "inferior (or inferiorly)" is used to indicate position of an item below a reference.

Figure 1:
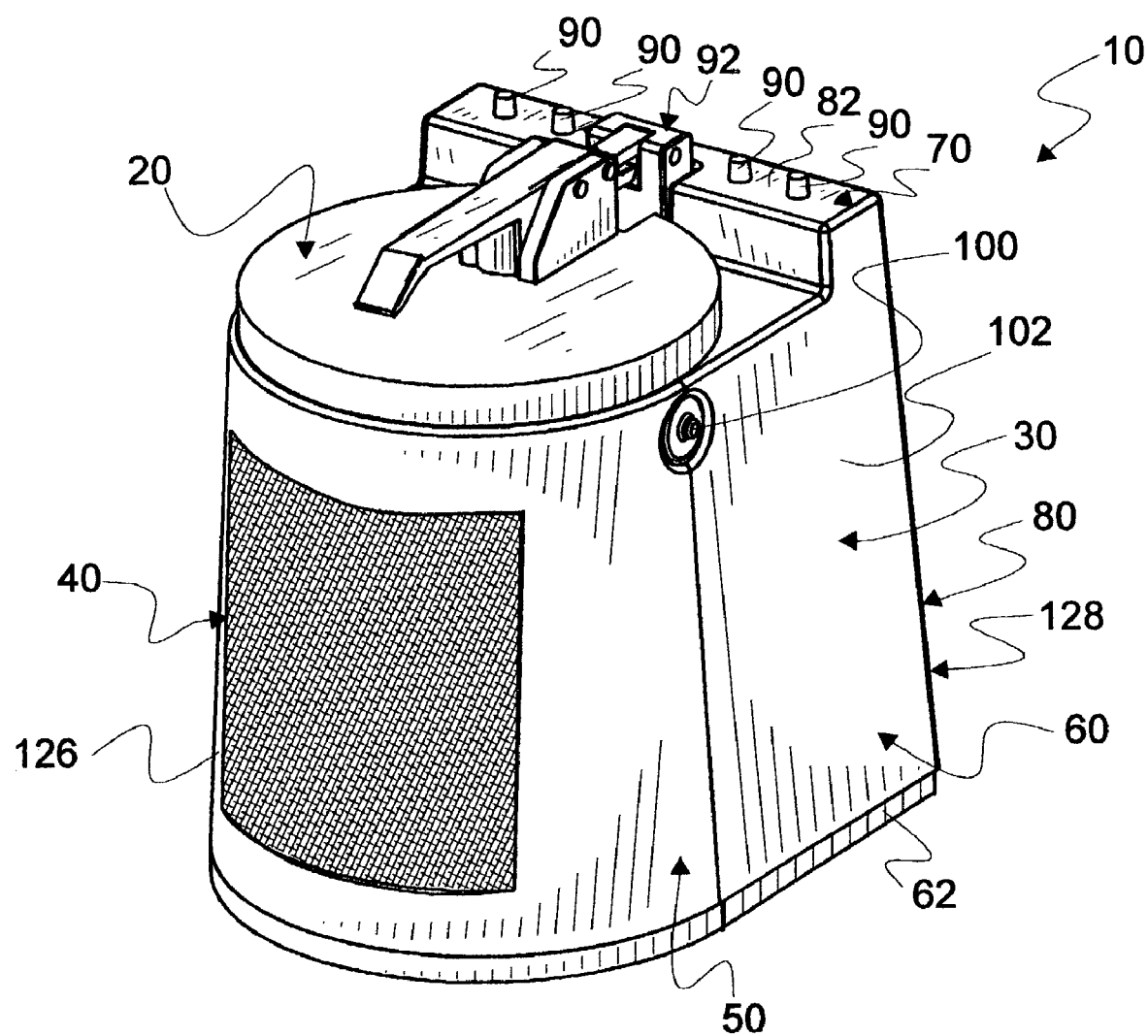
FIG. 1 is a perspective of an autoclave unit made according to the present invention.

An autoclave unit 10 made according to the present invention is seen in FIG. 1. Autoclave unit 10 generally comprises a removable lid 20, a housing 30; and a protective filter 40, disposed in a forward portion 50 of housing 30.

Housing 30 comprises a rearward portion 60, which rises superiorly relative to a base 62, to form a pedestal 70 along a backside 80. Disposed upon a top surface 82 of pedestal 70 is a plurality of status indicator lights, generally numbered 90. Medially disposed relative to indicator lights 90, along pedestal 70, is a latch assembly 92. A sterilizing cycle initiation switch 100 is superiorly disposed at a proximally seen side 102 of housing 30.

Figure 2:
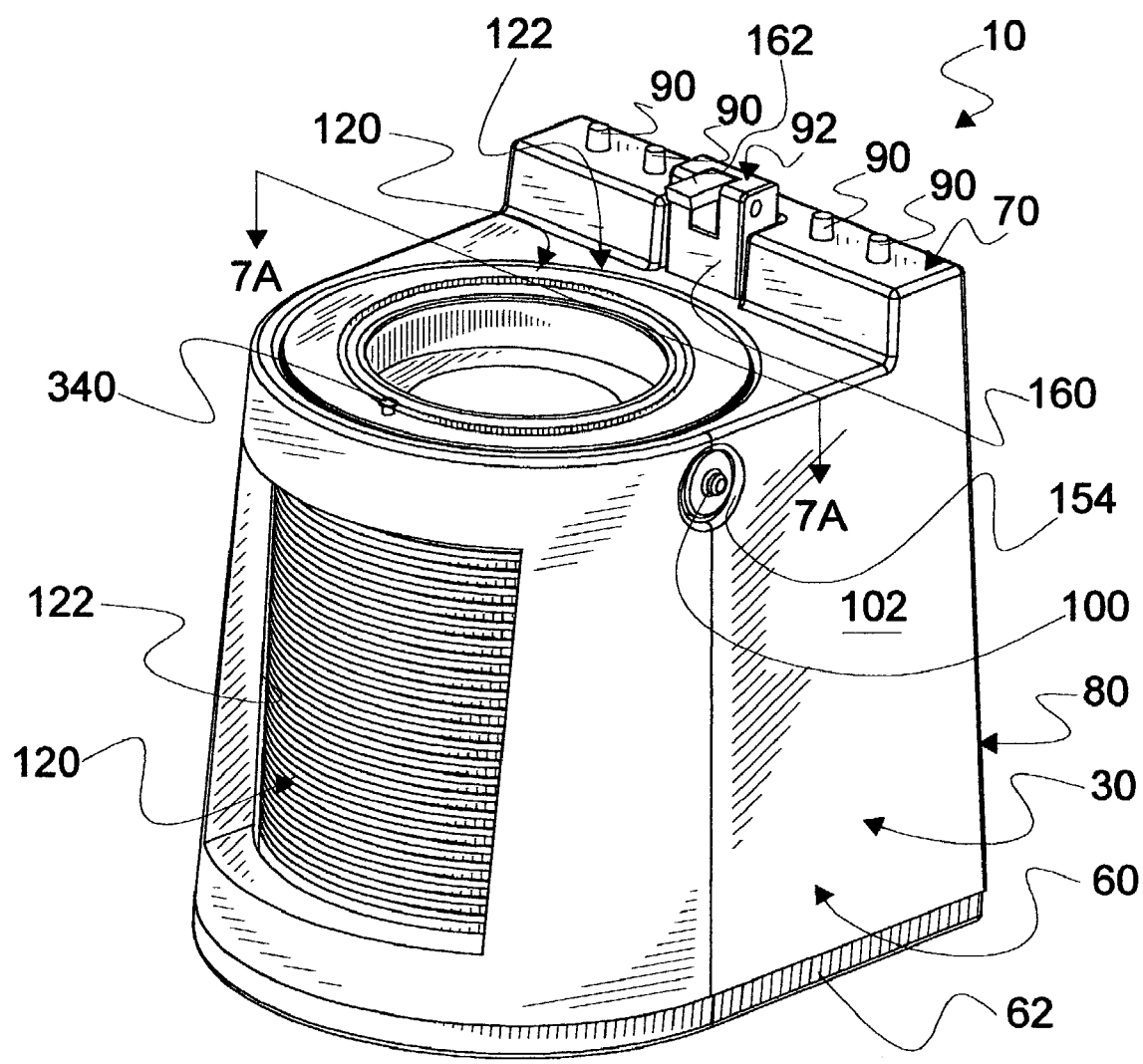
FIG. 2 is a perspective of the autoclave unit seen in FIG. 1 with a proximally disposed filter and a top lid removed.

Protective filter 40 and lid 20 are removed from autoclave unit 10 in FIG. 2 to reveal a vessel 120 disposed in a hollow interior 122 of housing 30. Major parts of unit 10 are seen in exploded format in FIG. 6 where unit 10 is seen to comprise lid 20, housing 30, filter 40, vessel 120, an associated gasket ("O" ring) 124 and a fan assembly 130. Base 62 is seen detached from housing 30. Dashed lines 132, 134, 136, 138 and 140 generally show relative direction for assembly and disassembly of respective filter 40, lid 20, fan assembly 130, vessel 120 and base 62 relative to housing 30. Gasket 124 is releasibly affixed to vessel 120 via dashed lines 142 and 144 as disclosed in detail hereafter. Generally, the site of filter 40 in unit 10 shall herein be referenced as the front side (or front 126, see FIG. 1); conversely pedestal 70 site of unit 10 shall herein be referenced as the back side (or back 128, also see FIG. 1) Wiring and electrical parts are not shown in FIG. 6 for clarity of presentation.

Figure 4:
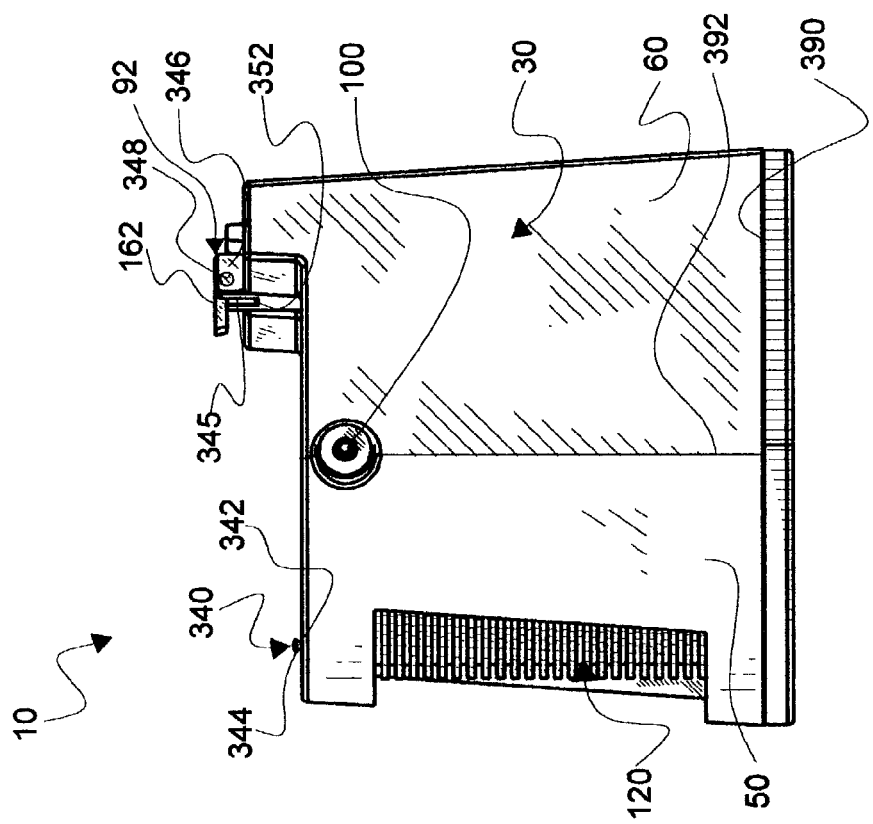
FIG. 4 is a lateral side view of the autoclave unit seen in FIG. 2.
Figure 3:
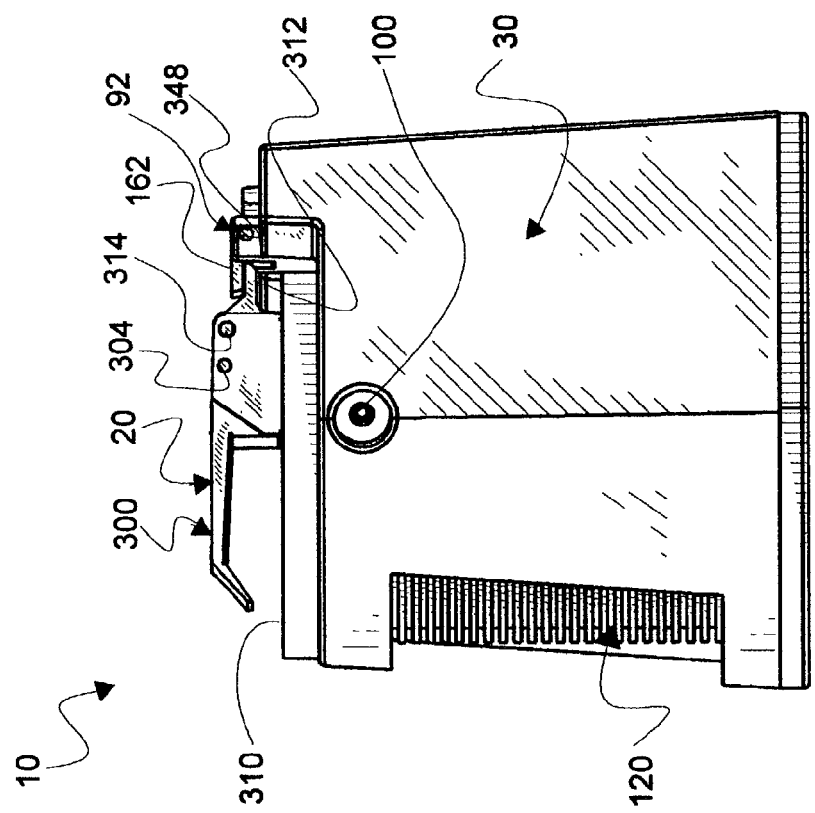
FIG. 3 is a lateral side view of the autoclave unit seen in FIG. 1.
Figure 5:
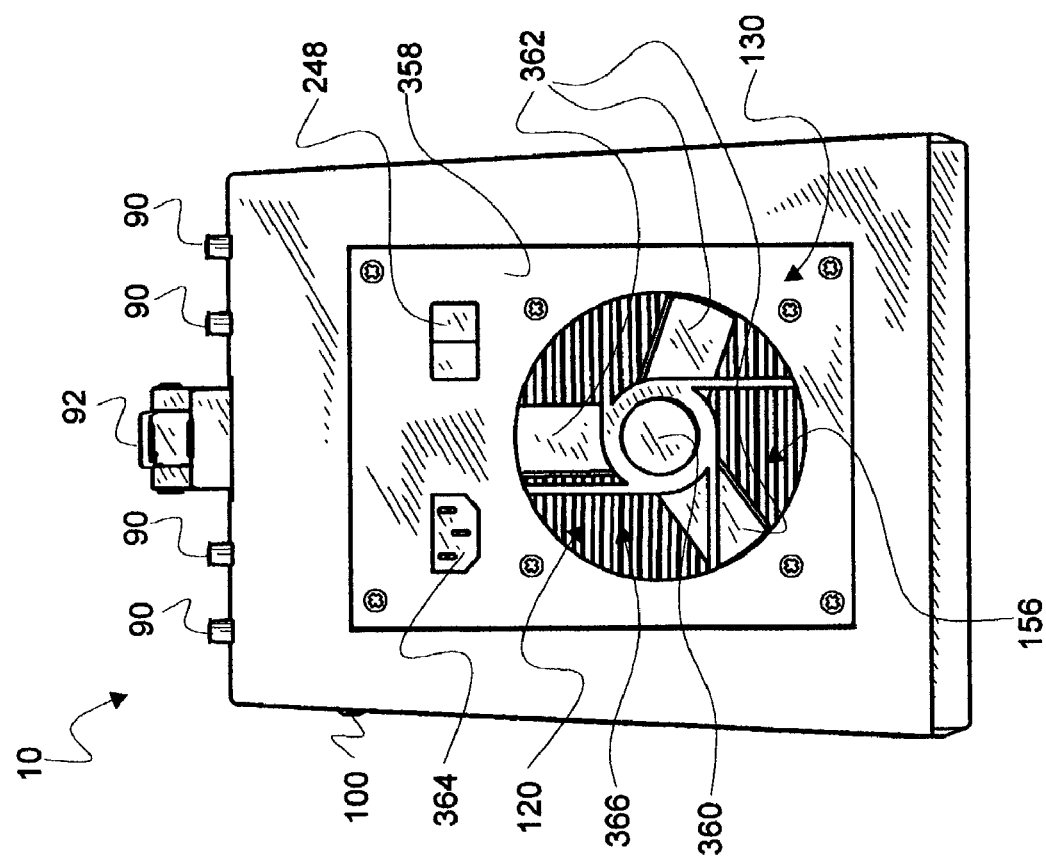
FIG. 5 is a back elevation of the autoclave unit seen in FIG. 1.
Figure 6:
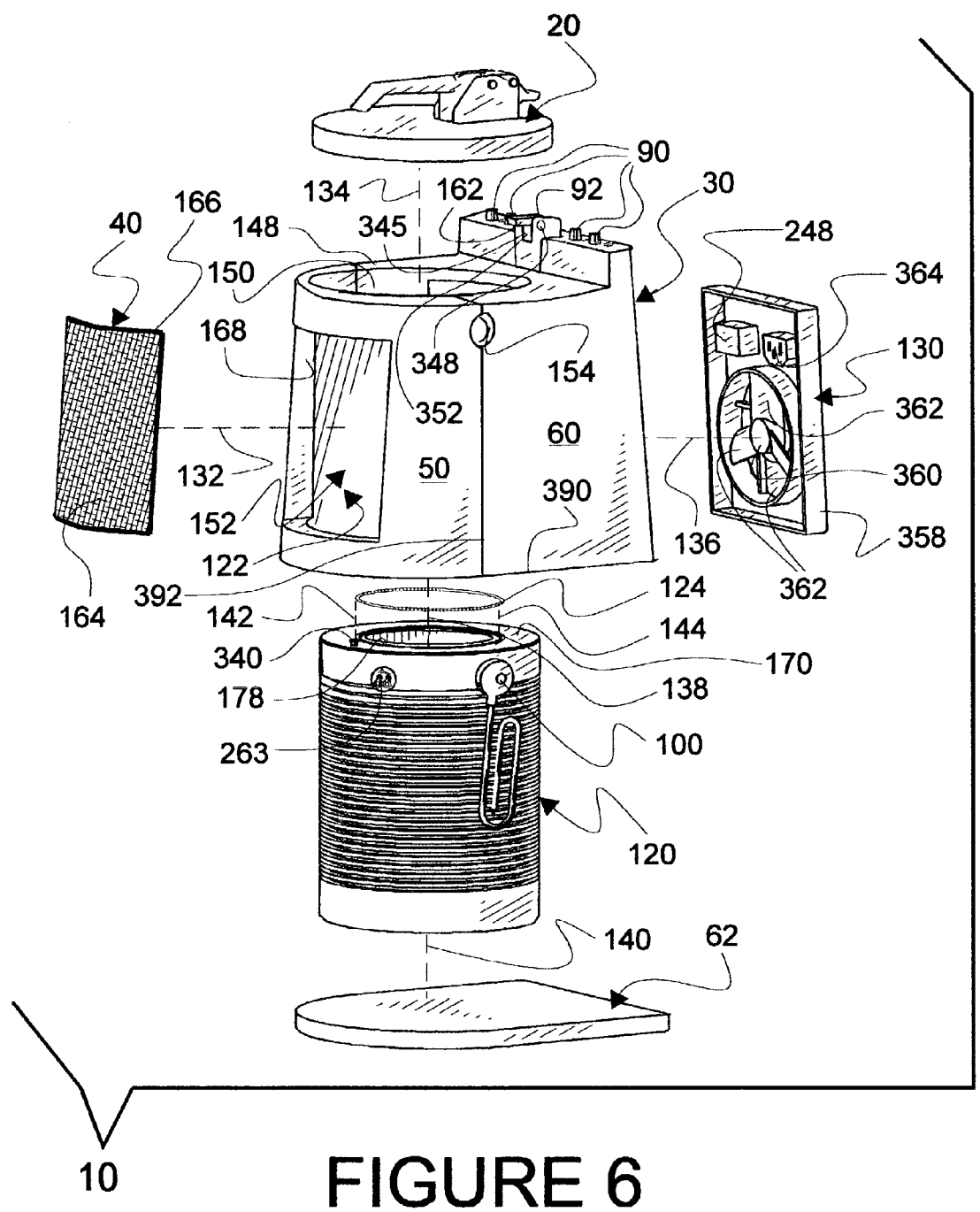
FIG. 6 is an exploded view of the autoclave unit seen in FIG. 1.

Housing 30 is seen in FIGS. 1-6. As seen in FIG. 6, housing 30 comprises hollow cylindrical interior 122 which conformably surrounds and protectively covers vessel 120 and associated electrical wiring and components (see FIG. 13). Housing 30 has a top planar surface 148 which has a large circular orifice 150 which provides ingress and egress access for items disposed in vessel 120 for sterilization. Ventrally or in a forward portion of housing 30, a second orifice 152 is sized and shaped for mounting of filter 40 and disposed for passage of air about vessel 120. A third orifice 154 provides an aperture for access to sterilizing cycle initiation switch 100. Still a fourth orifice 156, not totally seen in the figures, but seen partially covered by fan assembly 130 in FIG. 5 provides a second passage for air flow about vessel as disclosed in more detail hereafter.

As may be noted in FIG. 2, four smaller orifices (unnumbered) are disposed in pedestal 70 wherethrough indicator lights 90, for visual representation of operational status of unit 10, are installed. As disclosed in more detail hereafter, lights 90 may be individually colored to facilitate perception of operational status of unit 10. Latch assembly 92 has a forward face 160 and latch bar 162. Critical positions and functions of bar 162 are disclosed in more detail in following disclosure associated with fastening lid 20 against vessel 120. Latch assembly 92 is preferably made from a metal, such as anodized aluminum and is securely affixed to housing 30 through another aperture (also unnumbered), medially disposed along pedestal 70, as seen in FIG. 2. Parts for housing 30 may be machined or made by molding. Housing 30 may be made from urethane or other synthetic resinous material which is not deleteriously affected by vessel heating and which internally insulates for vessel 120 from ambient environmental temperatures and which provides a protective teal safety shield outside. Base 62 may be made from the same material as the rest of housing 30 and may be affixed thereto by mechanical or adhesive processes which are well known in the plastic assembly art.

Filter 40, which is seen disposed apart from housing 30 in FIG. 6, is preferably made from planar material 164 through which air and associated gases readily pass but which traps particulates being forced from interior 122 of housing 30 under pressure created by fan assembly 130. Note that filter 40 has an edge construction 166 which permits filter 40 to be compressively installed and retained by circumferential edges, generally number 168, disposed about orifice 152. As a practice, filter 40 should be regularly removed and cleaned or replaced. However, unit 10 should not be operated without having filter 40 in place, as protection provided against contact with vessel 120 during a sterilization cycle is considered to be an important safety measure.

Attention is drawn to FIGS. 2–9 and 14 wherein vessel 120 is variously seen. As seen in FIG. 2, vessel 120 is disposed for use within interior 122 of housing 30. Better seen in FIG. 7, vessel 120 comprises a planar top surface 170, a generally cylindrical external sidewall 174 and flat bottom 176. Surface 170 comprises a circular groove 178 which is sized and shaped to conformably and snugly accept an O-ring which forms gasket 124. Sidewall 174 comprises a series of grooves, generally numbered 180, which form a plurality of exposed ribs, generally numbered 182. Grooves 180 and ribs 182 combine to provide a relatively large surface area which facilitates cooling as ambient air passes thereover.

Figure 7:
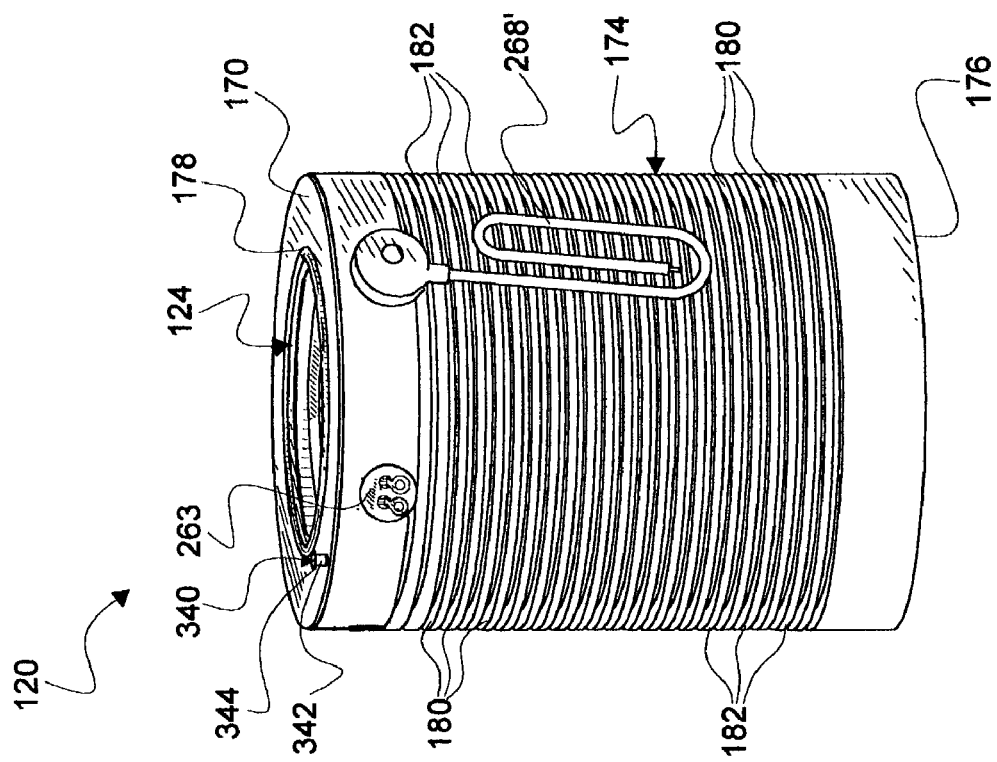
FIG. 7 is a perspective of a heating vessel which is a part of the autoclave unit seen in FIG. 2.
Figure 7A:
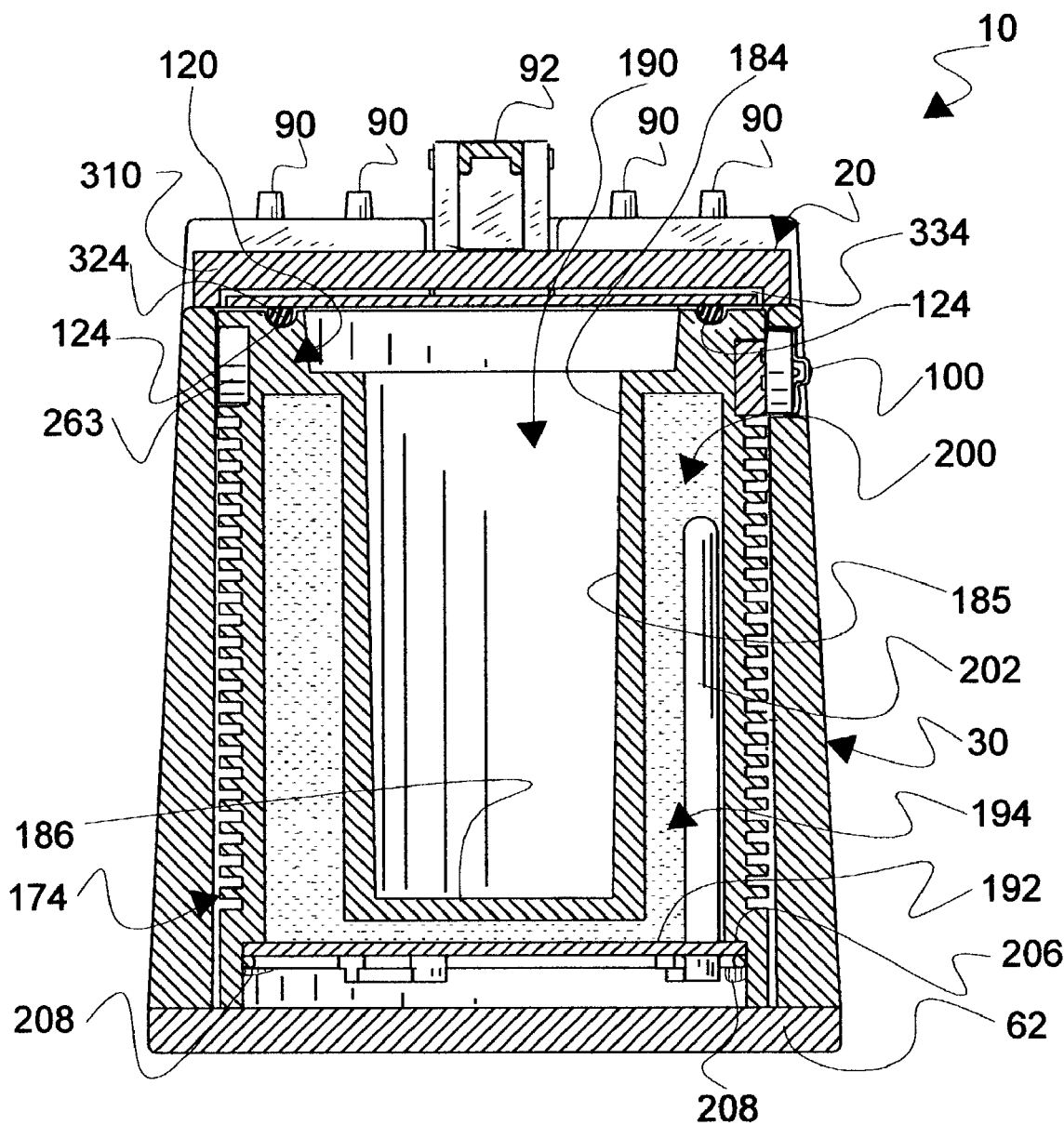
FIG. 7A is a cross section, of the heating vessel, made along lines 7A—7A in FIG. 2.
Figure 9:
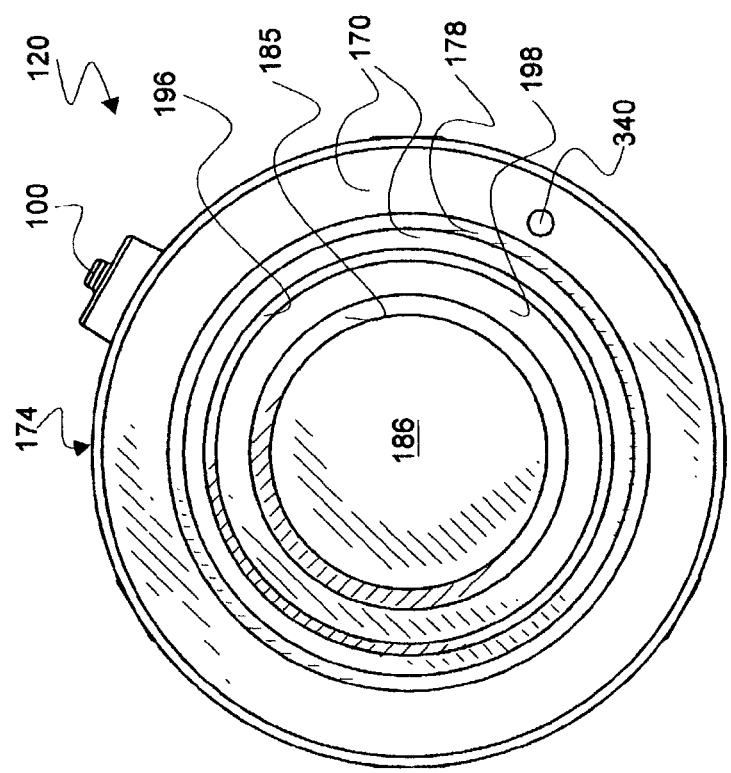
FIG. 9 is a top elevation of the heating vessel of FIG. 7.

As seen in cross section in FIG. 7A, vessel 120, disposed in housing 30, comprises an internally disposed, hollow structure 184 which has a cylindrical side 185 and a closed a bottom 186, thereby forming a well 190. Sidewall 174, structure 184 and an inferiorly disposed plate 192 cooperate to form a chamber 194 which is partially enclosed by side 185 and bottom 186 of well 190. Note that structure 184 should be designed for efficiently communicating heat from chamber 194 into well 190. Reference is made to FIG. 9 wherein a top view shows annular organization of vessel 120. Circular sidewall 174 bounds top surface 170. Top surface 170 is medially interrupted by groove 178 and then, more medially, by a descending circular wall 196 which may be seen due to draft. Wall 196 is abruptly ended inferiorly at a ledge 198 and is contiguous with side wall 185 of structure 184 (see FIG. 7A). Vessel 120 and plate 192 are preferably machined from aluminum.

Figure 8:
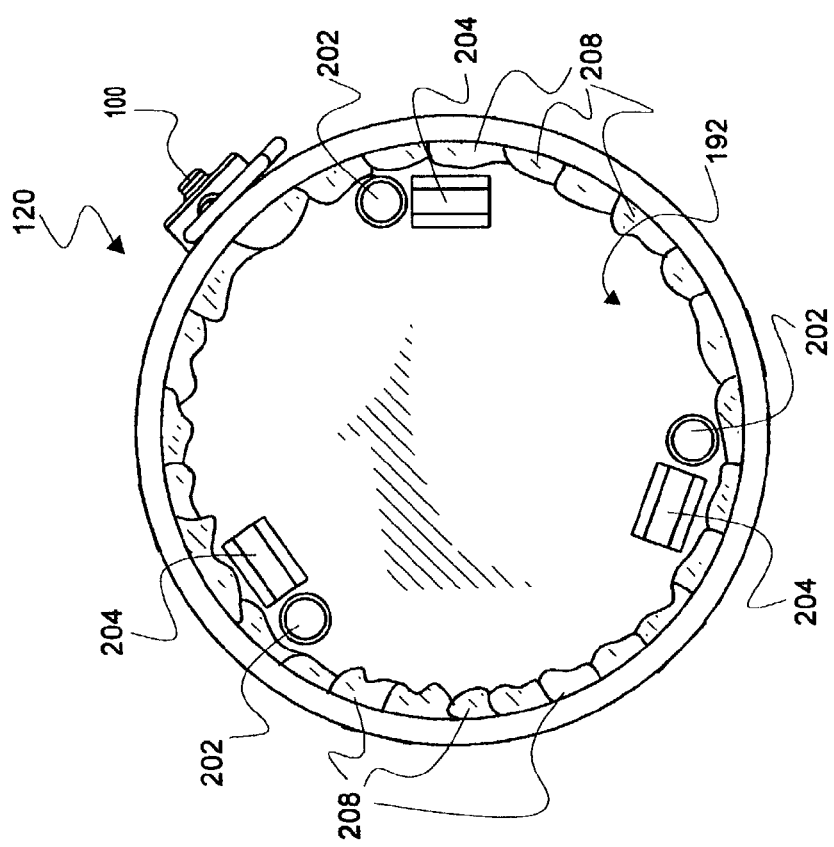
FIG. 8 is a bottom elevation of the heating vessel seen in FIG. 7.

Disposed within chamber 194 (as seen in FIG. 7A) is matter 200 which changes state at a predetermined temperature and at least one heating element 202 (in this embodiment, three such heating elements are employed). Disposition of the three elements, each numbered 202, are better seen in the exterior view of bottom plate 192 in FIG. 8. Note that bottom components seen m FIG. 8 are provided with wiring absent for clarity of presentation. A wiring diagram for all electrical components of unit 10 is provided in FIG. 13. Also seen in FIG. 8 are three low wattage heaters, generally numbered 204. To provide a pressure tight seal for chamber 194, plate 192 is secured to an inferiorly disposed surface ledge 206 of sidewall 174 (see FIG. 7A) via a series of weldments, generally numbered 208 (best seen in FIG. 8).

Volume of chamber 194 (and matter 200) is determined by a target sterilization temperature (and associated necessary time for adequate sterilization). As is well known in medical sterilization art, time to achieve adequate sterilization is a function of applied temperature. Generally, pressure is also considered as a factor, but it is well known that it is only incidentally significant. In a unit made according to the present invention, transfer of temperature generated in chamber 194 to items deposited for sterilization in well 190 is the critical variable. For this reason, design of unit 10 should provide for time to sterilize depending upon selected sterilization temperature as represented by example in Table 1.

TABLE 1

| Time to sterilize | Sterilization temperature |
| --- | --- |
| 20 minutes | 121° Centigrade |
| 10 minutes | 128° Centigrade |
| 3.5 minutes | 134° Centigrade |
| Nearly instantaneous | 141° Centigrade |

Figure 21:
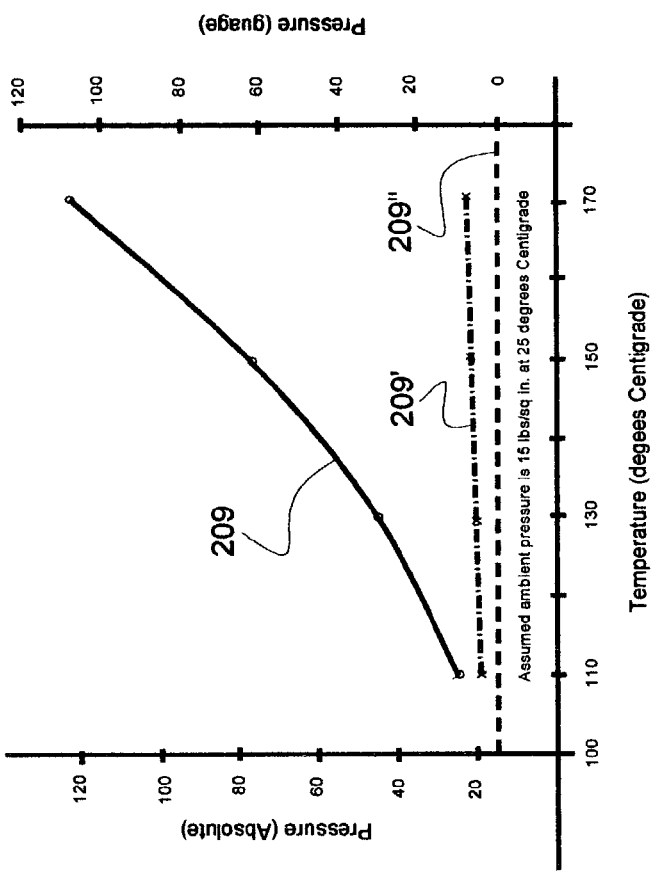
FIG. 21 is a graphic representation showing pressure versus temperature curves for a fixed volume chamber for a total pressure of air and supersaturated steam and just air captured in the chamber.

Of course, these times are only guidelines and, within the scope of the instant invention, pressures relating to temperatures in table 1 may be calculated with attention paid to ambient pressure by the graphical plot 209 seen in FIG. 21. FIG. 21 also provides a graph 209' of change in partial pressure versus temperature due to atmospheric gases. Plot 209" is assumed ambient pressure (in this example, 15 pounds per square inch). With efficient calorimetric communication between chamber 194 and well 190, items, including water, disposed within well 190 absorb heat from matter 200 to conformably lengthen or shorten the time period for sterilization as is disclosed hereafter.

Figure 13:
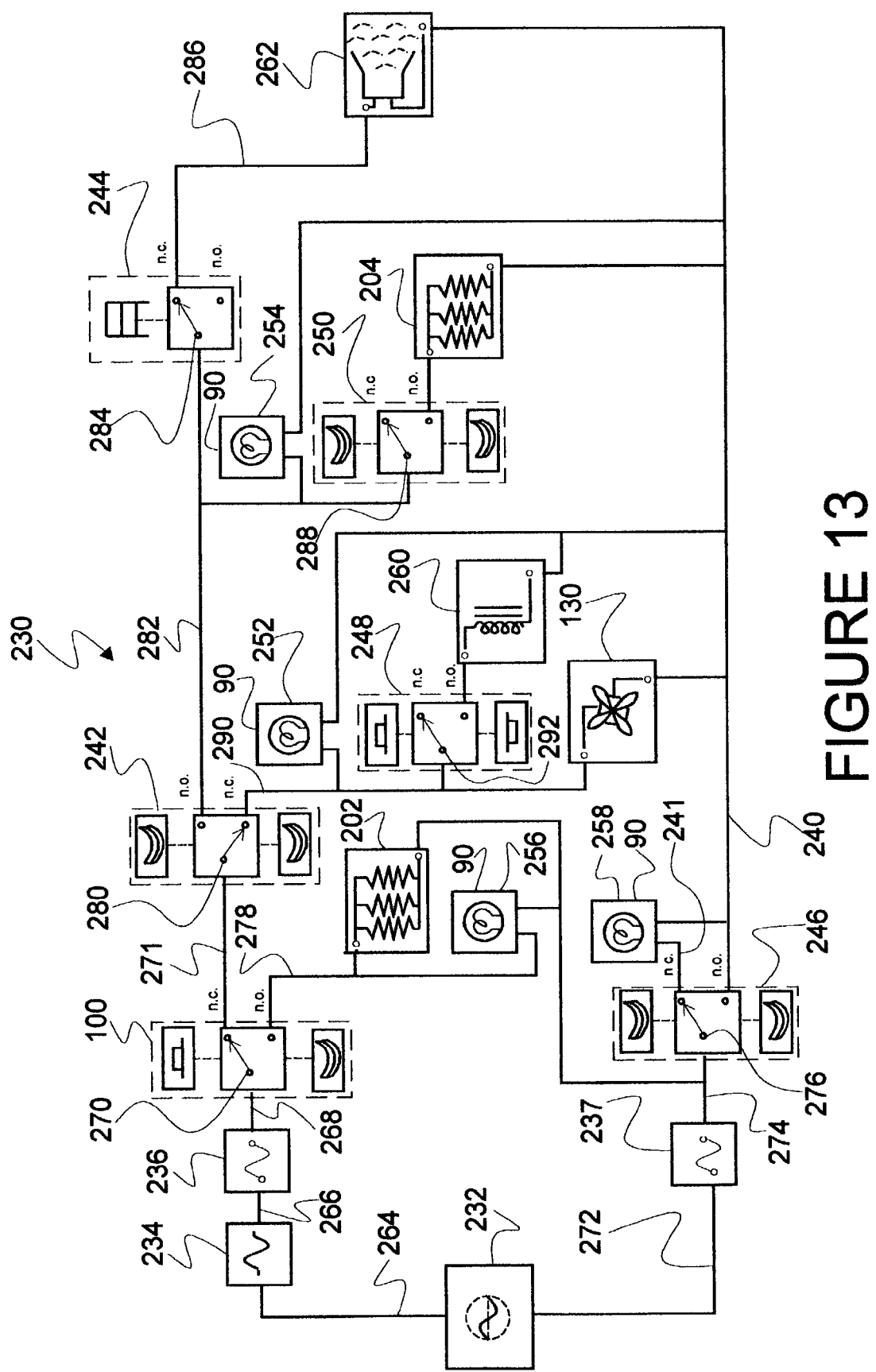
FIG. 13 is an electrical schematic circuit diagram of an electrical control system which is made according to the present invention and which may be used in the autoclave unit of FIG. 1.

Although timers, such as using electronic counters or timers or programmed computers, may be used to control any or all phases of a sterilization cycle, within the scope of the invention, it is currently preferred to employ electrical circuitry, an example of which is seen in FIG. 13, for controlling a unit 10 sterilization cycle. Various phases of operation of unit 10 may be visualized by reference to a graphical plot 210, seen in FIG. 14. Plot 210 represents temperature of matter 200 as a function of time during a sterilization cycle. Initial conditions (temperature) of matter 200 may vary, depending upon time since unit 10 was last used, but, in plot 210, an initial state at point 212 is assumed to be at a nominal room temperature of 20° Centigrade. Upon initiation of a sterilization cycle, heating elements 202 are powered and, based upon rate of heat generation by heating elements 202, temperature of matter 200 rises beyond a predetermined point 214 to a temperature at point 216 at which matter 200 fuses (i.e. changes state from a solid to a liquid). Matter 200 is selected from materials which remain at substantially the same temperature while undergoing fusion. As such, matter persists at the same temperature between points 216 and 218 (representing the time when all matter 200 has liquified). Once a complete state change occurs, temperature of matter 200 rises quickly as indicated between points 218 and 220. Note that the period between points 216 and 218 substantially represents a major portion of the unit 10 sterilization period and is basically dependent upon time required to fuse matter 200.

At point 220, power is removed from heating elements 202 and heat loss from matter 200 radiating from vessel 120 reduces temperature to a point 222, at which the unit 10 sterilization effectively ends. Detection of temperature reduction to point 222 results in activation of a cooling period during which rate cool of matter 200 (and contents of well 190) is accelerated until a temperature at point 224 is reached. At point 224, matter and items inside vessel 120 are sufficiently cooled to handle, permitting the cooling period to be terminated and, thereafter, parts to be removed with safety.

An example of controlling circuitry 230 for unit 10 is seen in FIG. 13. Note that there are no timing circuits (e.g. counters or other similar digital electronics) in circuitry 230. Circuitry 230 may be powered directly from a line power connection, such as a sixty cycle, 120 volt source 232, although other power sources may be used within the scope of the invention. As a safety precaution, circuitry 230 is provided with a power interrupter, such as a fuse 234. As a further safety precaution, a pair of thermal overload detectors 236 and 237 are used to provide a high temperature circuit breaker and thereby assure a secure limit to temperature of matter 200 (and therefore temperature and pressure in vessel 120). Circuitry 230 further is seen to comprise a plurality of switches including manually actuated and thermally reset single pole, double throw switch 100, a thermally actuated and reset single pole, double throw switch 242, a pressure actuated and reset single pole, single throw switch 244, a single pole, double throw thermally actuated switch 246, a thermally actuated single pole, single throw manually actuated switch 248 and a single pole, single throw thermally actuated switch 250. Exterior access to switch 248 is seen in fan assembly 130 in FIGS. 5 and 6. Four indicator lights, generally numbered 90, are identified as lights 252, 254, 256 and 258 to distinguish individual function and meaning. Circuitry 230 also includes heating elements, generally numbered 202 (which are also seen in FIGS. 7A and 8) and a second set of heating elements 204 (also seen in FIG. 8). Three other components of circuitry 230 are fan assembly 130 (also seen in FIGS. 5 and 6), pressure release solenoid assembly 260 and audio signal generator 262.

Thermally controlled switch 100 requires manual access through housing 30 as may be seen in FIGS. 1–4. As well, switch 100 is deeply imbedded into vessel 120 to provide caloric communication with matter 200. A pigtail wire 268', seen affixed to switch 100 in FIGS. 6, 7 contains wires 268, 271 and 278 as seen in FIG. 13. Pigtail wire 268 is shown as an integral part of switch 100. Other wiring is not shown for clarity of presentation of other parts. Other thermally controlled switches 242 and 246, generally numbered 263 in FIGS. 6, 7 and 7A, are also affixed to vessel 120 for caloric communication with matter 200.

To initiate operation, switch 100 is manually actuated, providing a source of power, via lines 264, 266 and 268 from source 232 to fuse 234 to detector 236 to pole 270 of switch 100, respectively. Note, return power is provided via line 272 through detector 237 and line 274 to pole 276 of switch 246 and therefrom through lines 240 and 241. Manual actuation of switch 100 resultingly delivers power through the normally open contact of switch 100 to line 278. Power on line 278 energizes heating elements 202 causing temperature to climb as indicated between points 212 to 214 of graph 210 seen in FIG. 14. Simultaneously, power is applied to indicator light 256 to provide a visual signal that a unit 10 heating cycle is in progress. Currently light 256 is a red light.

At a predetermined temperature before matter 200 reaches melting temperature, as indicated by point 214 of graph 210, switch 242 is thermally actuated although no power is provided to pole 280 until switch 100 is thereafter closed. Continued heating drives the temperature to point 216 of graph 210 at which fusion of matter 200 begins. As indicated by graph 210, temperature is substantially constant until matter 200 changes from solid to an entirely liquid state. When such occurs, a rapid temperature rise in matter 200 occurs as indicated by graph 210 between points 218 and 220. At the temperature of point 220, switch 100 resets removing power from heating elements 202 and turning off light 256. Power is then supplied through the normally closed contact of switch 100 through line 271 to pole 280 of switch 242 which already is in an actuated state, as earlier disclosed. For this reason, power is applied to the normally open contact of switch 242 along line 282 to pole 284 of switch 244.

Switch 244 is a pressure actuated switch which senses pressure within vessel 120. As is well understood in the art of steam autoclaving, desired effectiveness of sterilization can only be achieved by steam at a predetermined temperature which is directly associated with a given pressure. Independent of temperature of matter 200, well 190 and its contents must also be raised by calorimetric communication from chamber 194 to well 190. A clear indication of achieving a desired temperature within well 190 is via assurance that pressure in well 190 has exceeded a predetermined value during the sterilization period (i.e. at least by point 220 on graph 210). If switch 244 is not activated by pressure when power is applied to line 282, power is applied via line 286 to signal generator 262 which sounds an alarm.

At the same time power is applied to pole 284 of switch 244, power is also directed to turn on indicator light 254 to indicate a post heating element 202 powered phase of the sterilization cycle. Light 254 is currently an amber light. Concurrently, power is applied to pole 288 of switch 250. Switch 250 is bistable, switching to an open state at a nominal room temperature (e.g. 20° Centigrade) and closes at a cooler temperature (e.g. 10° Centigrade). As may be noted by graph 210, the sterilization phase is considered to extend effectively (with a predetermined lag time) from point 216 to point 222 as well 190 remains at an effective sterilization temperature through the entire period. If ambient air is at or below 10° Centigrade, cooling due to radiation from vessel 120 will shorten the sterilization phase unacceptably. For this reason a closed state of switch 248 while power is available at pole 288 activates heating elements 204 and slows cooling of matter 200 (and well 190) effectively lengthening the sterilization phase.

As earlier disclosed, the sterilization phase of unit 10 effectively ends at graph 210 point 222 (upon closure of switch 242). At such time, power is removed from line 282 turning off indicator light 254. Power is then applied to line 290, turning on indicator light 252 and actuating a cooling system (in this case turning on fan assembly 130). Also, power is applied to pole 292 of switch 248, providing opportunity for manual activation of pressure release solenoid 260 for more rapid cooling of well 190. Color of light 252 is chosen to be blue to indicate entry into a cooling phase of the sterilization cycle.

Switch 246 is a thermally actuated switch which opens at a nominal temperature between points 212 and 216 of graph 210 (see FIG. 14) and closes at a temperature at which items sterilized in unit 10 may be handled. Closure of switch 246 illuminates indicator light 258 when switch 100 and switch 242 are both closed. As such, illumination of indicator light 258 signals an end of the cooling phase, and therefore of the sterilization cycle, whereupon sterilized items may be removed from unit 10.

Depending upon important and primary safety considerations associated with pressure containment within vessel 120, fusion characteristics of matter 200 and sterilization temperature desired, parameters for thermal controlling devices disclosed above may be widely varied within the scope of the present invention. For example, found in following table 2 is a list of components which may be used for a unit 10 sterilize temperature of about 132° Centigrade.

TABLE 2

| \multicolumn{6}{c}{Thermally Controlled Switches} |
| Switch # | State | Temp. (° F.) | Temp. (° C.) | Part Numer | Company |
| --- | --- | --- | --- | --- | --- |
| 236, 237 | Open | 300 ± 7 | 149 ± 4 | TI INT08L-2326 | Texas Instruments |
|  | Close | None (manually operated) |  |  |  |
| 100 | Open | None (manually operated) |  | TI 4391513 | Texas Instruments |
|  | Close | 280 ± 10 | 138 ± 5 |  |  |
| 242 | Open | 260 ± 10 | 127 ± 5 | TI 4391-6* | Texas Instruments |
|  | Close | 230 ± 7 | 110 ± 4 |  |  |

TABLE 2-continued

| 246 | Open | 150 ± 10 | 66 ± 5 | TI4391-6* | Texas Instruments |
| --- | --- | --- | --- | --- | --- |
|  | Close | 125 ± 7 | 52 ± 4 |  |  |
| 248 | Open | 65 ± 5 | 18 ± 3 | TI4344-32-163 | Texas Instruments |
|  | Close | 50 ± 5 | 10 ± 3 |  |  |

| \multicolumn{5}{c}{Pressure Switch} |
| Switch # | State | Pressure (pounds/sq. in.) | Part Numer | Company |
| --- | --- | --- | --- | --- |
| 244 | Open | 40 | TI36PS44-1 | Texas Instruments |
|  | Close | 10 |  |  |

*Same part number, switching temperatues set at factory by specified order

Matter 200 may be any stable substance which changes state from a solid to a liquid and maintains a constant desired predetermined temperature during the state change. Particularly suited for use in unit 10 is paraffin. Paraffin may be formulated to accurately and precisely melt at a selected temperature between 100° C. and 170° C. Such paraffin is currently available from ASTOR Specialty Chemicals, 1600 Commerce, Marshall, Tex. 75670.

Pressure release solenoid 260 may be selected from a wide variety of manually operated pressure release solenoids currently on the market. Fan assembly 130 may be a cooling fan assembly which is commonly used in personal computers. Each heating element may be a 150 watt heater which operates on 110 volt A.C. power. Indicator lights for indicators 90 are widely commercially available as are signal generators for alarm indicator 262.

Reference is now made to FIGS. 1, 3, 4, 7A and 10–12 wherein lid 20 is seen. As seen in FIG. 1, lid 20 is closed over vessel 120 during a sterilization cycle to provide pressurized containment of steam generated therein. However, it is preferred, as seen in FIG. 4, that lid 20 be removed from vessel 120 such that clear access is provided to well 190 (see FIG. 7A). It is understood that clear access may be obtained by a hinged lid or a lid that otherwise may be tethered to vessel 120 or housing 30 and such lids are within the scope of the invention.

Figure 11:
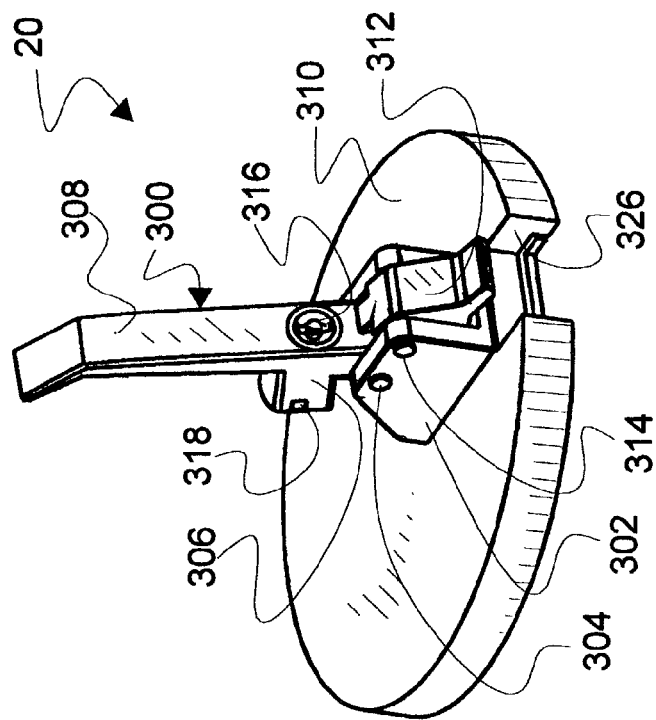
FIG. 11 is a perspective of the top lid seen in FIG. 10, but turned to show a rear side of a handle of the lid.
Figure 10:
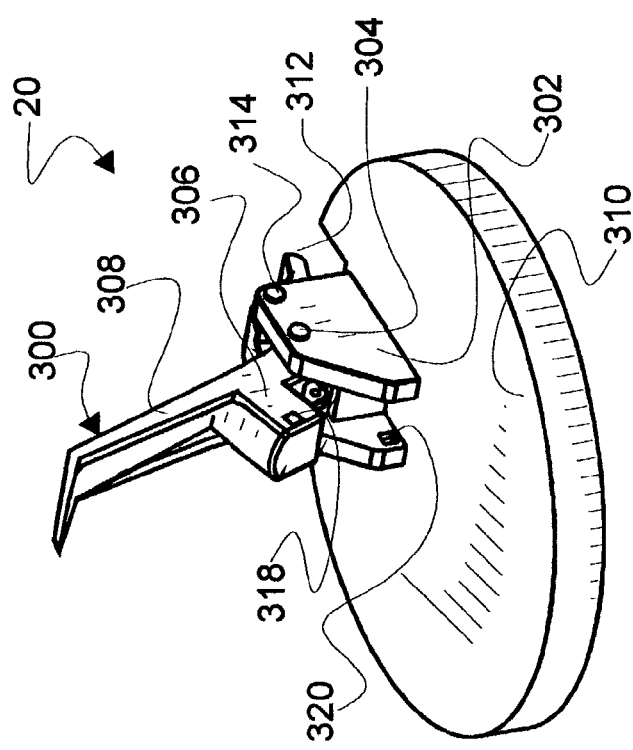
FIG. 10 is a perspective of a front facing top lid for the autoclave unit seen in FIG. 1, with a handle raised.
Figure 12:
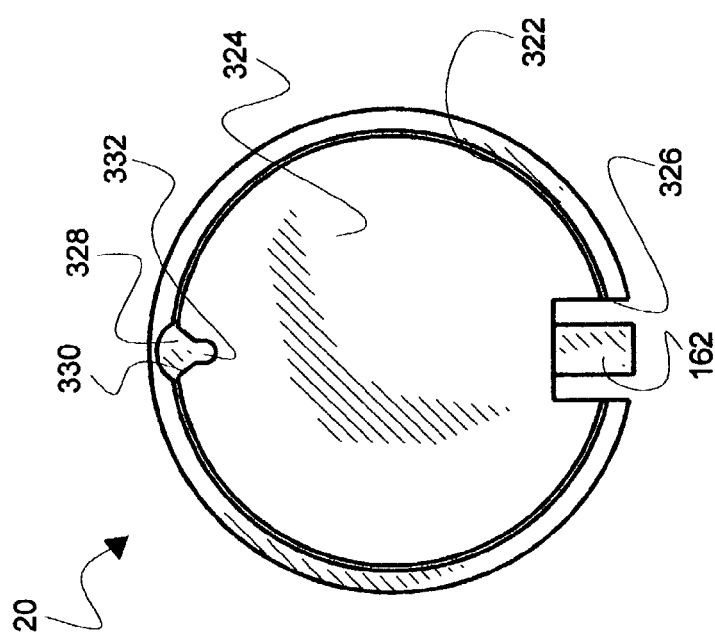
FIG. 12 is a bottom elevation of the top lid seen in FIGS. 10 and 11.

Lid 20 is best seen in FIGS. 10–12. Lid 20 comprises a rotatable handle 300 which is articulated to a support 302 by a shaft 304. Handle 300 may further comprise a lock compartment 306 (see FIG. 11) and a hand grip 308. Support 302 is securely affixed to a circular, planar base 310. Distally disposed relative to handle 300 is a latching component 312 which is articulated to support 302 by a shaft 314 which is substantially parallel to shaft 304. All parts of lid 30 must be sufficiently strong and rigid to provide an intractable seal against pressure created in vessel 120. For this reason, handle 300, latching component 312 and base 310 may be aluminum. Shafts 304 and 314 are preferably steel.

Handle 300 may comprise lock assembly 316 as best seen in FIG. 11. Lock assembly 316 comprises a pair of bolts 318 (only one of which is seen in FIGS. 10 and 11; the second bolt is juxtaposed visible bolt 318 in lock compartment 306). Each bolt 318 is disposed in a slot 320 (one of which is seen in FIG. 10), when handle 300 is rotated downward, lock assembly 316 is in position against base 310 and locked. As seen in bottom view of lid 20 in FIG. 12, base 310 comprises a hollow cylindrical bottom 322 in which a planar base plate 324 is securely affixed. Base 310 and base plate 324 cooperate to form a rearwardly disposed slot 326 sized and are positioned to permit slot 326 to be disposed about latch assembly 92 while lid 20 is being removed from contact with vessel 120.

Base plate 324 (with a portion of base 310) is seen to comprise a forwardly disposed slot 328. Slot 328 is formed to have an angulated open mouth 330 disposed toward front 126 (see FIG. 1) and a rearwardly disposed, more restricted closed groove 332. A space 334 is disposed between base plate 324 and base 310 as is best seen in FIG. 7A.

In cooperation with lid 20, elements of latching assembly 92 and vessel 120 are employed for securely, but releasably affixing lid 20 to seal well 190 of vessel 120. As seen in FIGS. 2, 4, 6 and 7, vessel 120 comprises an anchor pin 340 medially and frontally disposed in top surface 170. As best seen in FIG. 7, anchor pin 340 comprises a shaft 342, which is sized and shaped to facilely slide into groove 332 (see FIG. 12), and a flattened head 344 which is sized and shaped to fit through mouth 330 and into space 334, but which is lodged by groove 332.

Latching assembly 92 comprises bar 162 of a rotating assembly 345 being articulated to a supporting structure 346 by a shaft 348 (see FIG. 4). Assembly 345 is "L" shaped having horizontal portion 162 and a vertical portion 352. Note, that, as vertical portion 352 is rotated rearward, horizontal portion 162 is rotated downward toward base 310 when lid 20 is in place above vessel 120 (see, in particular, FIG. 3).

To releasably affix lid 20 to housing 30 and vessel 120, lid 20 is configured as seen in FIGS. 10 and 11, with handle 300 raised relative to base 310. Slot 328 is disposed about anchor pin 340 until head 344 lies within open mouth 330. Handle 300 is aligned with latching assembly 92 such that latching component 312 is inferiorly disposed relative to horizontal portion 162 and plate 324 is disposed upon gasket 124 (see FIG. 7A). Handle 300 is then rotated downward toward base 310 causing CAM/CAM action among handle 300, latching component 312 and rotating assembly 345 to force base 310 forward and lodge head 344 into groove 332 as latching component 312 is rotated upwardly against horizontal portion 162 to forcefully seal plate 324 against gasket 124 and, resulting, top surface 170 of vessel 120. Note that lock assembly 316 may be engaged and locked when handle 300 is so disposed for safety. To remove lid 20, handle 300 is simply raised and lid 20 is slid in a rearward direction until slot 328 releases anchor pin 340 so lid 20 maybe lifted from vessel 120.

Fan assembly 130 comprises a mounting frame 358 which is securely affixed to back 128 of housing 30, as seen in FIG. 5. As is also seen in FIG. 5, installed in frame 358 is a fan motor 360 and associated fan blades, generally number 362. A plug 364 provides a releasable connection for power to unit 10. A pathway 366 through orifice 156 for cooling air forced by action of fan assembly 130 across vessel 120 is best seen in FIG. 5. As disclosed previously, fan assembly 130 is activated by a cooling cycle initiated by closure of switch 242, see FIG. 13.

Figure 16:
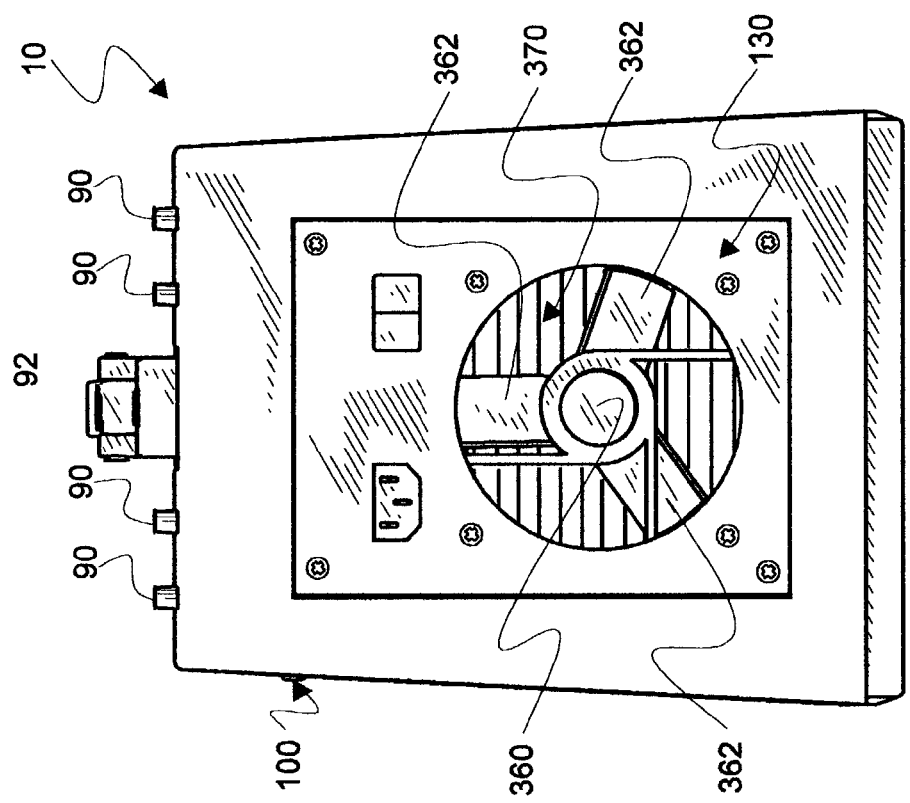
FIG. 16 is a back elevation similar to that seen in FIG. 5, but showing insulating shutters disposed behind a fan assembly.
Figure 17:
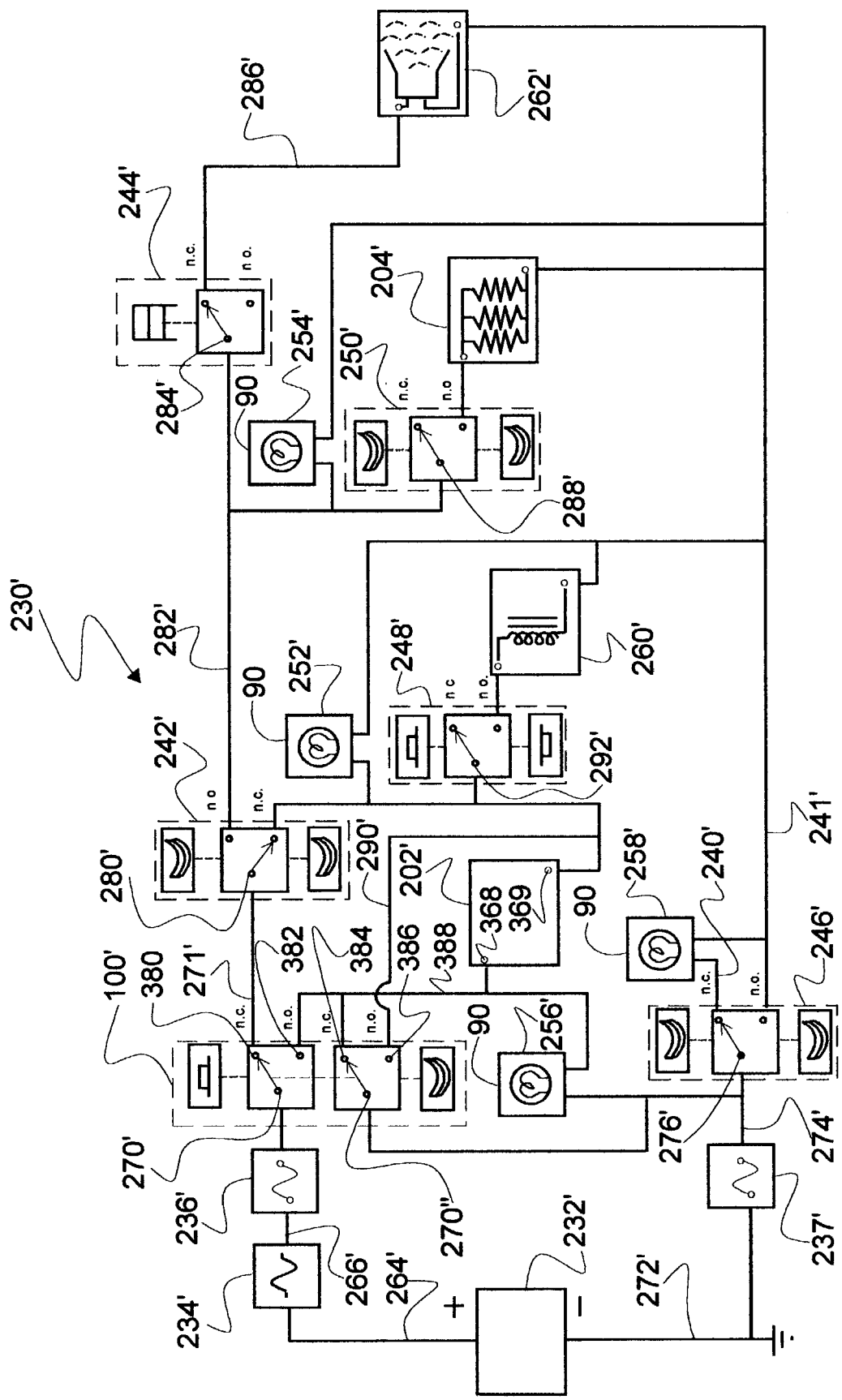
FIG. 17 is an electrical schematic diagram of an electrical control system similar to the electrical control system of FIG. 13, but utilizing an electronic heat pump for heating and cooling rather than heating tubes and a fan.

Referring once more to FIG. 14, a sterilization cycle may be shortened by improving efficiency of early heating, increasing effective sterilizing temperature (see table 1) or by accelerating cooling. Exemplary features which may effect shortening of sterilizing cycles are seen in FIGS. 15, 16 and 17. It is emphasized that such features and methods for shortening sterilizing cycles associated with FIGS. 15, 16 and 17 are not limited to examples provided herein, and other ways of shortening various periods of heating, sterilizing and cooling fill within the scope of the instant invention.

Figure 14:
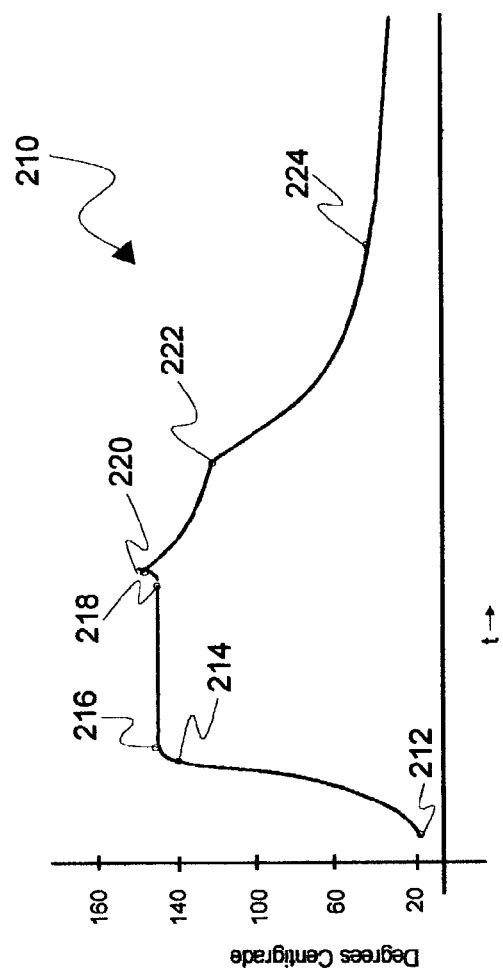
FIG. 14 is a graphical representation of exemplary temperature variation during an autoclaving cycle of the present invention.
Figure 15:
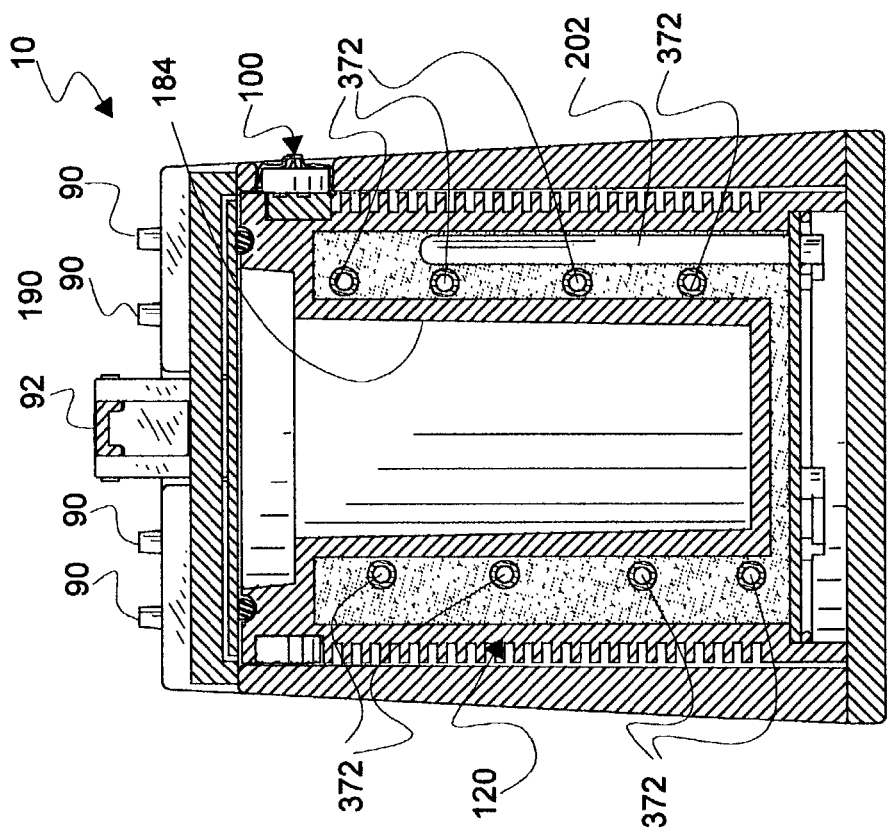
FIG. 15 is a cross section similar to the cross section seen in FIG. 7A, but showing cooling tubes disposed within the heating vessel.

As seen in FIG. 14, time from point 216 (when effective sterilization temperature is reached by matter 200) to point 222 (when forced cooling begins), may be conditionally shortened if the melting temperature of matter 200 is raised (See Table 1.) Similarly, rise time of temperature of matter 200 from starting temperature (point 212) to point 216 may shortened by using higher wattage heating elements 202 or by providing an environment which does not so readily lose heat from vessel 120 to the environment. Of course, the forced cooling cycle (beginning at point 222 and effectively ending at point 224) may be shortened by using more efficient cooling processes than air flow.

An example, seen in FIG. 16, employs louvers 370, interiorly disposed relative to fan assembly 130, which act to insulate vessel during heating and sterilization phases of the sterilizing cycle. Louvers 370 are hinged to open when fin motor 360 is actuated. Action of blades 362 force blow air toward and then through louvers 370 to accelerate cooling of vessel 120.

An example of accelerated cooling is seen in FIG. 15A cooling coil 372 is disposed in caloric communication with well 190 as well as with matter 200. Cooling devices which may be used to supply cooling fluid to coil 372 are well known in the refrigeration art. Control of such a cooling device (not otherwise shown) is provided between lines 278 and 240, wired either in parallel with or in place of fan assembly 130.

FIG. 17 is an example of a direct current powered control system circuit 230' having a DC power source 232'. Circuit 230' is similar in function to circuitry 230 with variations in parts due to basic power and operating considerations. For this reason, primes of numbers used in circuitry 230 are used for parts which are similar in function in circuit 230'. A first example of differences between circuitry 230 and circuit 230' is that circuit 230' has a DC power source 232' and circuitry 230 has an AC power source 232. Again, however, note that there are no timing circuits (e.g. counters or other similar digital electronics) in circuit 230'. Power source 232' may be a power supply powered directly from a line power connection, such as a sixty cycle, 120 volt source 232, although other power sources may be used within the scope of the invention. As a safety precaution, circuit 230' is provided with a power interrupter, such as a fuse 234'. As a further safety precaution, a pair of thermal overload detectors 236' and 237' are used to provide a high temperature circuit breaker and thereby assure a secure limit to temperature of matter 200 (and therefore temperature and pressure in vessel 120). Circuit 230' further is seen to comprise a plurality of switches including manually actuated and thermally reset double pole, double throw switch 100', a thermally actuated and reset single pole, double throw switch 242', a pressure actuated and reset single pole, single throw switch 244', a single pole, double throw thermally actuated switch 246', a thermally actuated single pole, single throw manually actuated switch 248' and a single pole, single throw thermally actuated switch 250'. Four indicator lights, generally numbered 90, are identified as lights 252', 254', 256' and 258' to distinguish individual function and signification. Circuit 230' also includes a heat pump 202' and a set of heating elements 204' (similar to elements 204 seen in FIG. 8). Note that fan assembly 130 of circuitry 230 is not seen in FIG. 17, as heat pump 202' provides both heating and cooling of matter 200, although a fan assembly, similar to fan assembly 130, may be used with circuit 230' within the scope of the invention to additionally accelerate cooling. Heat pump 202' has a first connection 368 and a second connection 369. Also seen in FIG. 17 are pressure release solenoid assembly 260' and audio signal generator 262'.

Thermally controlled switch 100' requires manual access through housing 30 as is seen for switch 100 in FIGS. 1–4 As well, switch 100' is deeply imbedded into vessel 120 to provide caloric communication with matter 200. Other thermally controlled switches 242' and 246', generally indicated by numbers 263 in FIGS. 6, 7 and 7A, are also affixed in vessel 120 for caloric communication with matter 200.

To initiate operation, switch 100' is manually actuated, providing a source of power, via lines 264', 266' and 268' from source 232' to fuse 234' to detector 236' and to pole 270' of switch 100', respectively. Pole 270' is associated with a normally closed contact 380 and a normally open contact 382 of switch 10'. Note, return power is generally provided via line 272' through detector 237' and line 274' to pole 276' of switch 246' and therefrom through lines 240' and 241'. However, also note that return power is provided to a pole 270" of switch 100', and that pole 270" is associated with normally closed contact 384 and normally open contact 386. Thus, when switch 100' is open, return power is supplied to a line 290' and therefore to second connection 369 of heat pump 202'. At the same time, source power is applied from contact 382 through line 388 to first connection 368 of heat pump 202' to provide heating to matter 200, causing temperature to climb as indicated between points 212 to 214 of graph 210 seen in FIG. 14. Simultaneously, power is applied to indicator light 256' to provide a visual signal that a unit 10 heating cycle is in progress. Currently light 256' is a red light.

At a predetermined temperature before matter 200 reaches melting temperature, as indicated by point 214 of graph 210, switch 242' is thermally actuated although no power is provided to pole 280' until switch 100' is thereafter closed. Continued heating drives the temperature to point 216 of graph 210 at which fusion begins. As indicated by graph 210, temperature is substantially constant until matter 200 changes from solid to an entirely liquid state. When such occurs, a rapid temperature rise in matter 200 occurs as indicated by graph 210 between points 218 and 220. At the temperature of point 218, switch 100' resets removing power from heat pump 202' and turning off light 256'. Note that return power is then provided to first connection 368 via line 388 and normally closed contact 384. Power is then supplied through the normally closed contact 380 of switch 100' through line 271' to pole 280' of switch 242' which already is in an actuated state, as earlier disclosed. For this reason, power is applied to the normally open contact of switch 242' along line 282' to pole 284' of switch 244'.

Switch 244' is a pressure actuated switch which senses pressure within vessel 120. As is well understood in the art of steam autoclaving, desired effectiveness of sterilization can only be achieved by steam at a predetermined temperature which is directly associated with a given pressure. Independent of temperature of matter 200, well 190 and its contents must also be raised by calorimetric communication from chamber 194 to well 190. A clear indication of achieving a desired temperature within well 190 is via assurance that pressure in well 190 has exceeded a predetermined value during the sterilization period (i.e. at least by point 220 of graph 210). If switch 244' is not activated by pressure when power is applied to line 282', power is applied via line 286' to signal generator 262' which sounds an alarm.

At the same time power is applied to pole 284' of switch 244, power is also directed to turn on indicator light 254' to indicate a post powered heating phase of the sterilization cycle. Light 254' is currently an amber light. Concurrently, power is applied to pole 288' of switch 250'. Switch 250' is bistable, switching to an open state at a nominal room temperature (e.g. 20° Centigrade) and closing at a cooler temperature (e.g. 10° Centigrade). As may be noted by graph 210, the sterilization phase is considered to extend effectively (with a predetermined lag time) from point 216 to point 222 as well 190 remains at an effective sterilization temperature through the entire period. If ambient air is at or below 10° Centigrade, cooling due to radiation from vessel 120 will shorten the sterilization phase unacceptably. For this reason a closed state of switch 248' while power is available at pole 288' activates heating elements 204' and effectively slows cooling of matter 200 (and well 190) effectively lengthening the sterilization phase.

As earlier disclosed, the sterilization phase of unit 10 effectively ends at graph 210 point 222 (upon closure of switch 242). At such time power is removed from line 282' turning off indicator light 254'. Power is then applied to line 290', turning on indicator light 252' and actuating a cooling system (in this case reversing power to heat pump 202' with return power being provided through via normally closed contact 384 of switch 100'). Also, power is applied to pole 292' of switch 248', providing opportunity for manual activation of pressure release solenoid 260' for more rapid cooling of well 190. Color of light 252' is chosen to be blue to indicate entry into a cooling phase of the sterilization cycle.

Switch 246' is a thermally actuated switch which opens at a nominal temperature between points 212 and 216 of graph 210 (see FIG. 14) and closes at a temperature at which items sterilized in unit 10 may be handled. Closure of switch 246' illuminates indicator light 258' when switch 100' and switch 242' are both closed. As such, illumination of indicator light signals an end of the cooling phase, and therefore of the sterilization cycle, whereupon sterilized items may be removed from unit 10.

As earlier indicated, depending upon important and primary safety considerations associated with pressure containment within vessel 120, fusion characteristics of matter 200 and sterilization temperature desired, parameters for thermally controlled devices disclosed above may be widely varied within the scope of the present invention. For example, while components listed in table 2 are associated with circuitry 230, other components which may be used in circuit 230' are currently commercially available.

Figure 20:
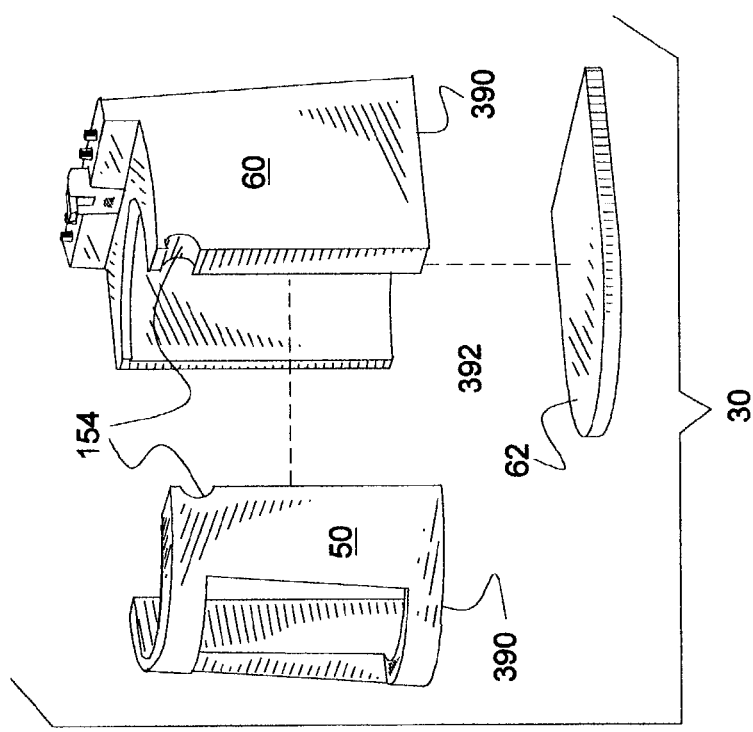
FIG. 20 is an exploded view of a housing according to the invention.
Figure 24:
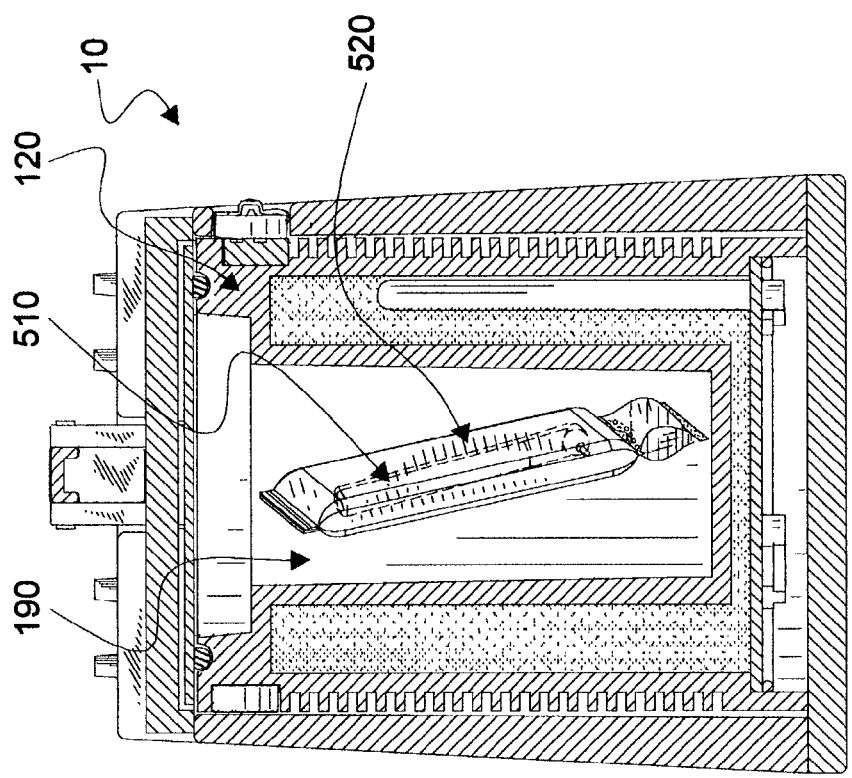
FIG. 24 is a cross section similar to the cross section seen in FIG. 7A with the sterilization bag seen in FIG. 23 disposed in a well of the heating vessel and the item seen in FIG. 22 disposed within the sterilization bag.

Reference is made to FIG. 20 which provides an alternate method for assembling housing 30 such that switch 100 of vessel 120 may be readily accessible through orifice 154. It should be noted that a channel (not shown) may be made from a baseline 390 about a line 392 where rearward part 60 joins forward part 50 (see FIGS. 4 and 6) thereby permitting parts 50 and 60 to be made as a single part. However, as seen in FIG. 20, parts 50 and 60 may be made separately and mechanically or adhesively joined to permit vessel 120 (and therefore switch 100 to be captured within orifice 154 at time of assembly. In both cases, base 62 is mechanically affixed to parts 50 and 60 after installation of vessel 120. Currently, base 62 is preferably affixed to parts 50 and 60 with screws.

A remarkable feature of the present invention is the opportunity for a source of steam (i.e. water) to be disposed in vessel 120 along with items to be sterilized as unit 10 is temperature controlled rather than pressure controlled and steam is internally generated rather than being introduced from an external source. That internally disposed source is generally provided within vessel 120 along with items to be sterilized. Examples of various modes are seen in FIGS. 18, 19 and 23–28, although many other forms and modes may be used within the scope of the invention.

Figure 19:
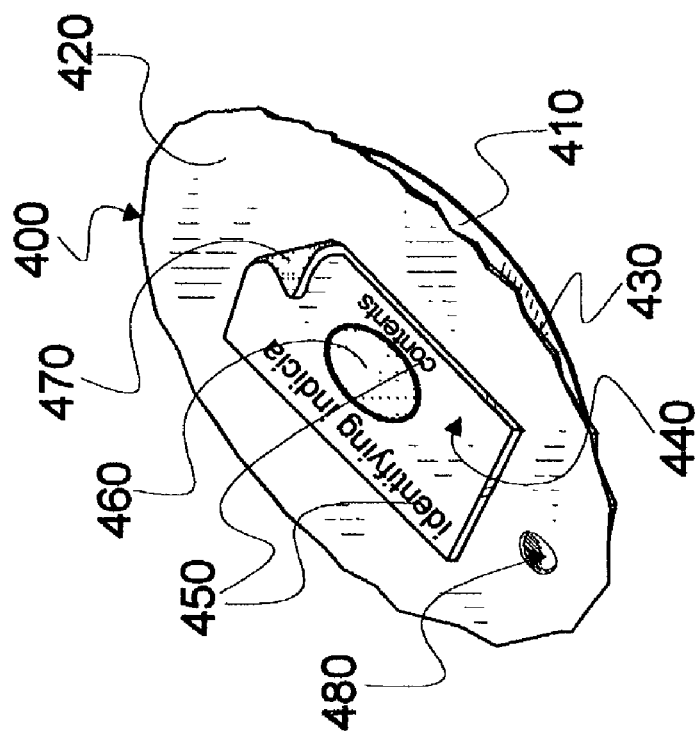
FIG. 19 is a perspective of the capsule seen in FIG. 15, but having been collapsed under pressure whereby water was expelled into a heated well of the vessel.
Figure 18:
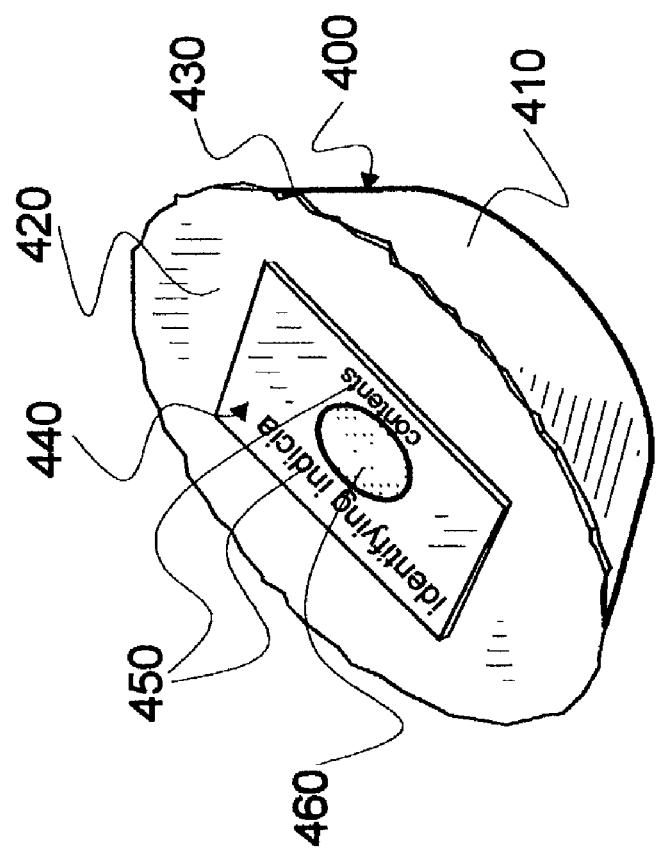
FIG. 18 is a perspective of a water containing capsule which may be used for a source of water in a vessel of an autoclave unit made according to the present invention.

As seen in FIGS. 18 and 19, water may be provided within a puncturable capsule or container 400. As seen in FIG. 18, capsule 400 has a frustum shaped bottom 410 having an attachable superiorly disposed lip (not shown) whereat a top 420 is adhesively or otherwise affixed to provide a seal 430 for water. Base material for bottom 410 and top 420 may be polypropylene, although any material which provides a non-contaminating container for water and which is not adversely affected by temperatures and steam to produce deleterious contaminates during autoclaving may be used. Water is preferably ultra-pure water having a specific conductance of less than or equal to 0.055 micromhos/centimeter), although water of other purity may be used within the scope of the invention.

Affixed to top 410 is a label 440 which may comprise identifying indicia, generally numbered 450, and an ink spot 460. Ink spot 460 is preferably made by ink which changes color at a temperature which is consistent with sterilizing temperatures. Such inks are currently commercially available. Also label 440 is preferably affixed to top 410 by an adhesive backing 470 (see FIG. 19) which permits label 440 (with color changed ink showing effect of passing through sterilizing temperatures) to be removed and affixed to a record for tracking purposes.

Water from capsule 400 may be displaced for steam generation in well 190 by piercing of capsule 400 (see hole 480 in FIG. 19) as an operating procedure when loading items into well 190 preparatory to beginning an autoclaving cycle. However, since a very large pressure is produced by heated water (see plot 209 of FIG. 21), seal 430 may be designed to break as a result of an increased internal capsule 400 pressure produced when capsule 400 is heated within well 190.

Figure 25:
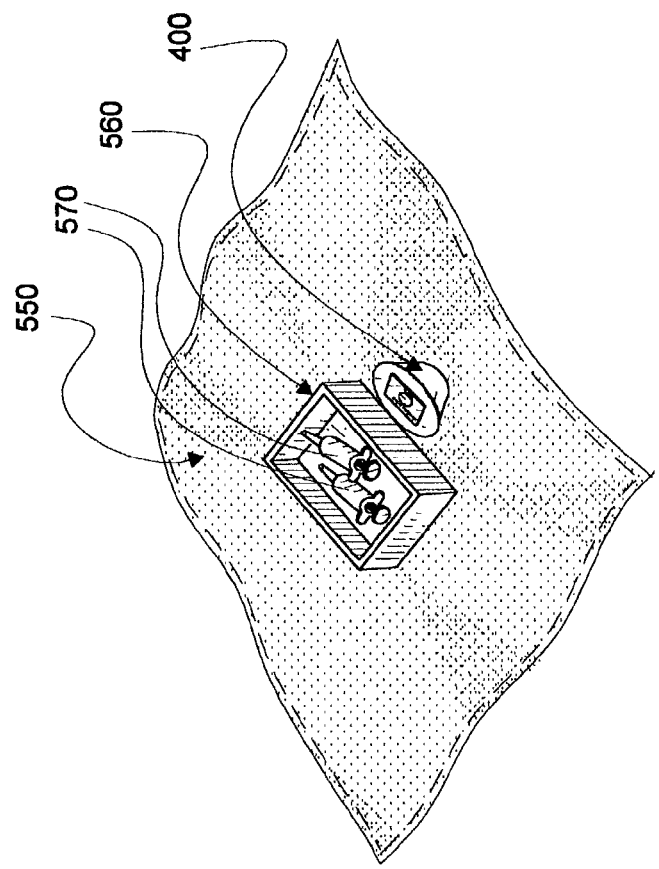
FIG. 25 is a perspective view similar to FIG. 2 with a sharps container being displaced into an autoclave unit along with a capsule which provides a source of water for autoclaving operation.

A remarkable opportunity to improve safety of handling filled sharps containers may be accomplished by operating procedures associated with unit 10. As an example, FIG. 25 shows a used sharps container 500, already filled with contaminated sharps, being displaced into well 190 of vessel 120 along with a water containing capsule 400, note arrow 502. As most sharps containers are made from polypropylene, processing of sharps container 500 (and like sharps containers) through an autoclaving cycle does not deleteriously affect the container which may be used as a transporter before, during and after sterilizing variously contaminated contents of the container. Note that unit 10 may be made in various sizes and shapes permitting adaption of the vessel 120 well (e.g. well 190) to sharps container dimensions. Once sterilized, disposal of the sharps container and its contents may follow disposal processes which are simpler, safer and of lower cost than required methods for disposing of contaminated sharps.

Figure 22:
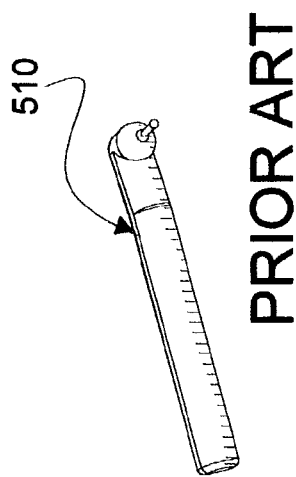
FIG. 22 is a perspective of a sample item to be sterilized.
Figure 23:
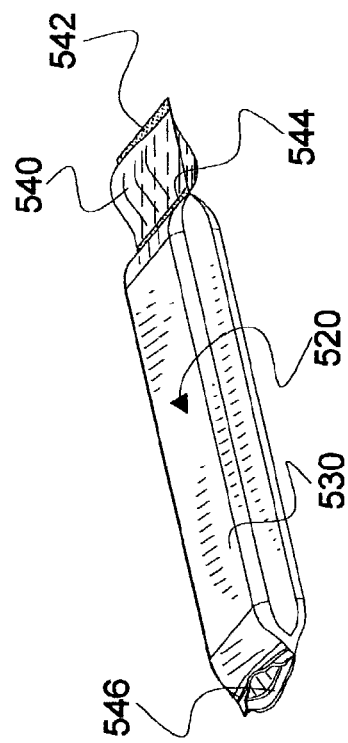
FIG. 23 is a perspective view of a sterilization bag according to the present invention.

Sterilizing parts for reuse provides an opportunity for dramatically reducing costs of acquiring new parts. Methods for sterilizing parts for reuse are shown in FIGS. 22, 23 and 26–28 An exemplary prior art part 510 to be sterilized is seen in FIG. 22. A bicompartmental bag 520 is seen in FIG. 23. Bag 520 has a parts compartment 530 and a water containing compartment 540. Further, bag 520 comprises a first end seal 542, an inter compartment seal 544 and a manually accessible closure 546 at a second end. Closure 546 may be a zipper locking type seal. Seal 544 is designed to perforate due pressure raised within compartment 540 before seal 542 is separated. In this manner, water contained in compartment 540 is delivered as steam and steam producing water to compartment 520. Bag 520 with exemplary part 510 enclosed therein is seen disposed in well 190 of vessel 120 for autoclaving in FIG. 24. Note that bag 520 provides a protective enclosure for sterilized parts when removed from unit 10 after autoclaving. 544 and a manually accessible closure 546 at a second end. Closure 546 may be a zipper locking type seal. Seal 544 is designed to perforate due pressure raised within compartment 540 before seal 542 is separated. In this manner, water contained in compartment 540 is delivered as steam and steam producing water to compartment 520. Bag 520 with exemplary part 510 enclosed therein is seen disposed in well 190 of vessel 120 for autoclaving in FIG. 24. Note that bag 520 provides a protective enclosure for sterilized parts when removed from unit 10 after autoclaving. Bag 520 may be made from polypropylene or other material which may be used as a water container and which withstands autoclaving temperatures, see Table 1.

Figure 26:
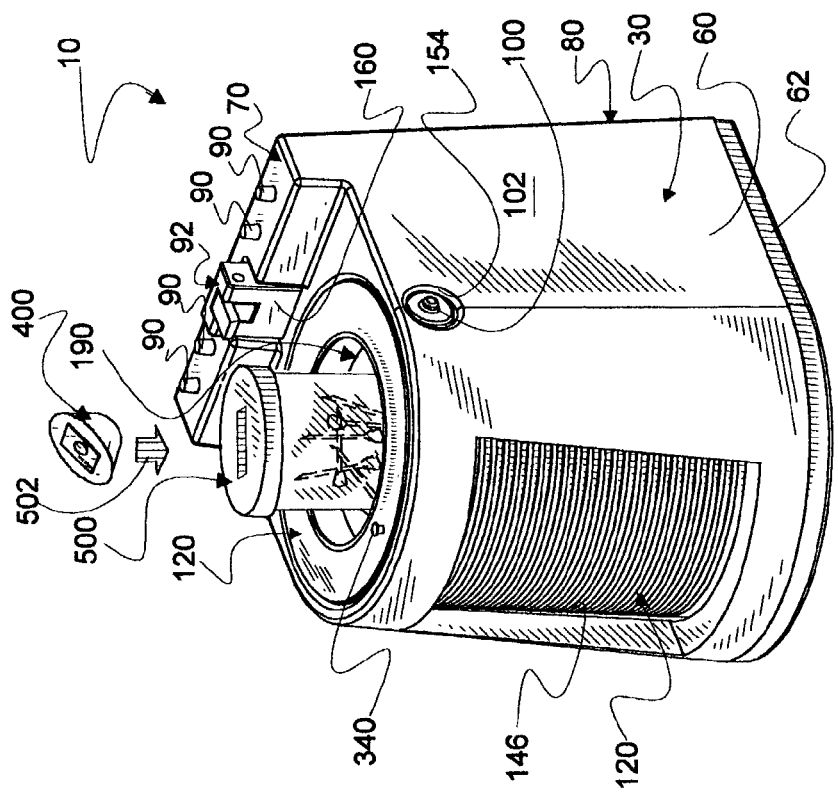
FIG. 26 is a perspective of items including a tray of parts to be sterilized, a capsule for providing a source of water for autoclaving operation and a wrap in which the parts are sterilized and protected thereafter.
Figure 28:
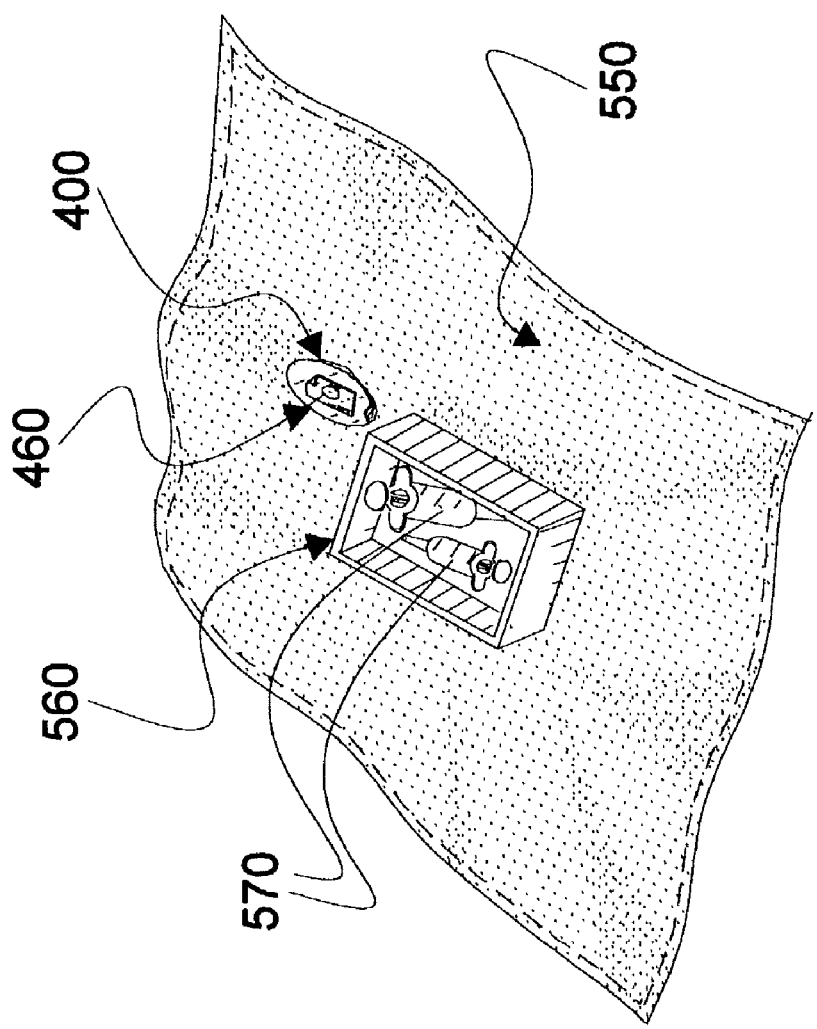
FIG. 28 is a perspective similar to FIG. 26, but after autoclaving swing a capsule.
Figure 27:
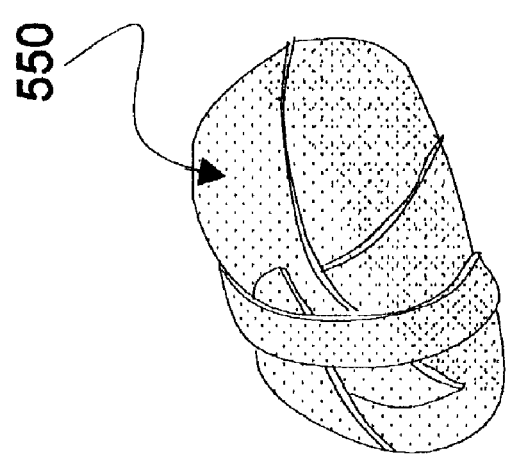
FIG. 27 is a perspective wherein the parts and capsule seen in FIG. 26 are enclosed by the warp preparatory to autoclaving.

It is common for items to be wrapped and sterilized and delivered for use in a medical procedure in the wrap to assure delivery of sterile product. An effective method for autoclaving items disposed in a sterile wrap is seen in FIGS. 26–28. As seen in FIG. 26, a wrap 550, a tray 560 containing items, generally numbered 570, and a water containing capsule 400 are collected preparatory to being sterilized. Wrap 550 is tightly bundled about tray 560, items 570 and capsule 400 as seen in FIG. 27 and placed in unit 10 for autoclaving. After autoclaving and delivery for a medical procedure, wrap 550 is unbundled as seen in FIG. 28. Note, evidence of adequate sterilization is provided by a compressed capsule 400 and color charged ink spot 460.

Attention is drawn to FIGS. 29–38 wherein containers made according to the preset invention are disclosed. The container seen in FIG. 29 is similar to container 500 and is therefore referenced by number 500'. Container 500' comprises a body 580 and an attachable lid 582 and is generally identified by a label 584 having identifying indicia 586 printed thereon. Note that it is a safety practice to provide a biohazard warning on the label. While such a biohazard warning is not shown, it is required for sharps containers sold and used in the United States.

Container 500' is sized and dimensioned to fit inside a well 190 of an autoclave unit 10 for sterilizing contents of container 500'. Ink for indicia 586, used on label 584, may be similar to ink used on spot 460 (see FIGS. 18 and 19) which changes color as a result of passing through an autoclaving cycle to provide a visual indication of container and container contents status.

As seen in FIG. 31, body 580 comprises a hollow cylindrical sidewall 588 closed by a substantially flat bottom 590 to define a hollow interior 592. Superiorly and externally, sidewall 588 comprises a superiorly disposed, external section 594 which is has an exterior thread 596 whereby lid 582 may be securely hut releasibly affixed.

Lid 582 comprises a closed planar top 598 which is contiguous with a descending lip 600. Internally lip 600 comprises a thread 602 which is sized and dimensioned to accommodate thread 596 to facilitate fixing lid 582 to body 580. Top 598 has a planar interior surface 604 to which a ring 606 of synthetic resinous material is affixed.

Generally, lid 582, except for ring 606, and body 580 may be injection molded from a material, such a polypropylene, which can meet criteria for safely containing sharps stored therein and which is substantially structurally unchanged while undergoing a sterilization cycle during autoclaving, such as in unit 10. However, ring 606 is made of a material which melts or otherwise becomes somewhat fluid during an autoclaving cycle. Because the temperature of unit 10 is precisely maintained during autoclaving, as earlier disclosed, a material may be selected which will become fluid during predetermined portions of the sterilization cycle (e.g. between points 214 and 218 of graph 210 as seen in FIG. 14). Such a material is urethane.

As seen in FIG. 32, ring 602 has changed state during sterilization and has flowed from surface 604 into contact with lip 600 and sidewall 588 to provide a seal 608 in the vicinity of threads 596 and 602. Such a seal may be a locking seal which securely affixes lid 582 to body 580 or may be a hermetic seal. It is important to note that if seal 608 is a hermetic seal, a pathway for passage of gas between well 190 and hollow interior 592 must be available until temperature inside unit 10 reaches an equilibrium temperature, at least until point 216 of graph 210, see FIG. 14.

As seen in FIG. 30 a material which is ultra-adsorbent is seen to be a circular disk 609 which is sized and shaped to fit upon bottom 590 inside interior 592. See FIG. 31. Such a material is used to collect and contain condensed water at the end a sterilization cycle to minimize undesirable discharge of fluid from a sterilized container. Such a material may be an absorbent pad available commercially as Dry-Mop® Laminate Sheets, available from Multisorb Technologies, 325 Harlem Road, Buffalo, N.Y. 14224-1893.

Water for sterilizing items within container 500' may be added into well 190 of unit 10 prior to initiating a sterilization cycle or into interior 592 when gas transfer pathways between interior 592 and well 190 exist prior to point 216 of graph 210, seen in FIG. 14. Otherwise, water should be added both to well 190 and to interior 592 separately.

Reference is now made to FIG. 33 wherein a lid 610 is affixed to body 580 to form a container 500". Lid 610 comprises a lip 600' which is similar in form and function to lip 600. However, a top surface 612, which is inwardly contiguous with lip 600', is medially interrupted by a recessed region 614. Region 614 is further interrupted by a rectangular opening 616, through which used sharps are discarded into interior 592 (see FIG. 32). It may noted that no sharps are seen in FIGS. 31, 35 and 36. Inclusion of images of discarded sharps has been avoided for a clearer presentation of the containers, themselves.

Sharps are discarded through opening 616 past an obstructing barrier 618. In presently available sharps containers, barriers, such as barrier 618, are often canted inwardly and downwardly to oppose a direct line of travel of sharps disposed in interior 592 outwardly through opening 616. In other sharps containers a hingeable opening may be utilized to provide added security from inadvertent expulsion of items from the container.

A water containing capsule 620 formed and dimensioned to fit withing region 614 is seen in FIG. 34. Capsule 620 is similar to capsule 400 having a frustum shaped water containing bottom part 622 (note capsule 620 is inverted in FIG. 34). However, on a top lid portion 624, a ring 626 of synthetic resinous material is securely affixed. Material for ring 626 should meet requirements of ring 606, previously described. Note that before displacing container 500" into a unit 10, capsule 620 is displaced to reside within region 614. If desired, capsule 620 may be snap fit into region 614. In such a case, care must be taken as earlier disclosed to assure a pathway for water vapor and other gasses. If such does not exist, water should be added to well 190, as well.

Inverted top lid portion 624 is seen to have a weakened segment 628 in FIG. 35. Pressure developed during a sterilization cycle causes segment 628 to burst and release water from capsule 620 into interior 592 and therefrom into well 190. (For relative disposition of container 500" in unit 10, see displacement of container 500 into well 190 in FIG. 25.)

Due to water vapor and other gas pressure exerted during autoclaving, capsule 620 is collapsed as seen in FIG. 36. Note that material from ring 626 has flowed through opening 616 to affix capsule 620 to lid 610. Also, as seen similarly in FIG. 32, material of ring 626 is seen to flow into threads of body 580 and lip 600' to form a locking seal in FIG. 36.

In those cases where water is deposited into an interior of a container, such as container 500" seen in FIG. 38 (and into a well 190) prior to autoclaving, a stopper, such as stopper 630, may be used to provide a protective closure over an item insertion orifice, such as opening 616 (seen in FIG. 33). Stopper 630 is seen in FIG. 37 to comprise a sealing ring 632, which is similar in form and function to ring 626 (see FIG. 34). Sealing ring 632 is affixed to an underside or contact side 633 of a planar disk 634 of stopper 630. Disk 634 may be sized and dimensioned to snap into region 614 of lid 610. Note that, for convenience, stopper 630 may be affixed by a tether to container 500". Also, alternatively, a capsule may be displaced into container 500" to provide a water source.

The invention may be embodied in other specific forms without departing from the spirit or essential characteristics thereof. The present embodiment is therefore to be considered in all respects as illustrative and not restrictive, tie scope of the invention being indicated by the appended claims rather than by the foregoing description, and all changes which come within the meaning and range of equivalency of the claims are therefore intended to be embraced therein.

The invention claimed is:

1. A self-contained, single manual step unit for thermally sterilizing dental and medical instruments and other contaminated items comprising:
   an insulating and protective housing comprising an orifice for ingress and egress of items to be sterilized;
   a vessel disposed within said housing which comprises an inner contiguous vertical wall, which is closed at the bottom to form a medially disposed well wherein items are sterilized and cooled thereafter, and unobstructed at the top which provides an accessible opening through said orifice;
   said unit further comprising a thermal regulation assembly disposed in caloric communication with said vessel, said assembly comprising an inner wall and a juxtaposed outer wall separated therefrom and sealed thereto to form a chamber;
   said thermal regulation assembly further comprising a cooling subassembly having a cooling coil disposed in caloric communication with said thermal regulation assembly inner wall;
   a predetermined quantity of matter, which changes state at a predetermined temperature which is consistent with sterilizing, hermetically sealed within said chamber;
   a disengageable lid which covers, protects and seals said accessible opening when engaged and which permits access to said well when disengaged;
   at least one heater disposed in caloric communication with said matter, said heater having adequate thermal output to heat the matter in excess of the change-of-state temperature of the matter;
   a source of water disposed within the well, at least a portion of which is transformed to steam as part of the sterilization cycle; and an electrical control system which limits duration of the sterilization cycle and automatically initiates a cooling cycle at the end of the sterilization cycle.

2. A self-contained, single manual step unit for thermally sterilizing dental and medical instruments and other contaminated items according to claim 1 wherein said inner contiguous vertical wall and said thermal regulation assembly inner wall are the same wall.

3. A self-contained, single manual step unit for thermally sterilizing dental and medical instruments and other contaminated items according to claim 1 further comprising a container in which items to be sterilized are loaded and displaced into the vessel well.

4. A self-contained, single manual step unit for thermally sterilizing dental and medical instruments and other contaminated items according to claim 3 wherein said container is plastic.

5. A self-contained, single manual step unit for thermally sterilizing dental and medical instruments and other contaminated items according to claim 4 wherein said plastic container is a sharps container.

6. A self-contained single manual step unit for thermally sterilizing dental and medical instruments and other contaminated items according to claim 5 wherein said plastic container comprises deposits of synthetic resinous material disposed to melt during sterilization and thereby be displaced to provide a seal.

7. A self-contained single manual step unit for thermally sterilizing dental and medical instruments and other contaminated items according to claim 6 wherein said seal is a locking seal.

8. A self-contained single manual step unit for thermally sterilizing dental and medical instruments and other contaminated items according to claim 6 wherein said seal is a hermetic seal.

9. A self-contained single manual step unit for thermally sterilizing dental and medical instruments and other contaminated items according to claim 6 wherein said synthetic resinous material is urethane.

10. A self-contained, single manual step unit for thermally sterilizing dental and medical instruments and other contaminated items according to claim 1 wherein said electrical control system comprises at least one unit status indicator light.

11. A self-contained, single manual step unit for thermally sterilizing dental and medical instruments and other contaminated items according to claim 10 wherein said at least one status indicator light comprises a red "heater on" indicating light.

12. A self-contained, single manual step unit for thermally sterilizing dental and medical instruments and other contaminated items according to claim 10 wherein said at least one status indicator light comprises a blue "cooling cycle in progress" indicating light.

13. A self-contained, single manual step unit for thermally sterilizing dental and medical instruments and other contaminated items according to claim 10 wherein said at least one status indicator light comprises a green "sterilization cycle complete" indicating light.

14. A self-contained, single manual step unit for thermally sterilizing dental and medical instruments and other contaminated items according to claim 1 wherein said electrical control system comprises an audio signal to provide a low pressure warning.

15. A self-contained, single manual step unit for thermally sterilizing dental and medical instruments and other contaminated items according to claim 1 wherein said matter is paraffin.

16. A self-contained, single manual step unit for thermally sterilizing dental and medical instruments and other contaminated items according to claim 1 wherein said source comprises a perforateable capsule.

17. A self-contained, single manual step unit for thermally sterilizing dental and medical instruments and other contaminated items according to claim 16 further comprising a medical wrap which protectively encloses said capsule and items to be sterilized and which is disposed in said well throughout the sterilization cycle.

18. A self-contained, single manual step unit for thermally sterilizing dental and medical instruments and other contaminated items according to claim 1 wherein said source is a packet formed in a plastic bag.

19. A self-contained, single manual step unit for thermally sterilizing dental and medical instruments and other contaminated items according to claim 18 wherein said capsule contains ultra pure water.

20. A self-contained, single manual step unit for thermally sterilizing dental and medical instruments and other contaminated items according to claim 1 wherein said capsule comprises a mark made of matter which noticeably changes color when a adequate sterilization cycle has been completed.

21. A self-contained, single manual step unit for thermally sterilizing dental and medical instruments and other contaminated items according to claim 20 wherein said mark is disposed upon a removable label whereby an indicator of completion of a sterilization cycle is readily transferred from the capsule to a reference log.

22. A self-contained, single manual step unit for thermally sterilizing dental and medical instruments and other contaminated items according to claim 1 wherein said electrical control system comprises a first temperature sensitive switch which is in caloric communication with said matter and which resets to an open state to end the heating portion of the sterilization cycle when said matter reaches a predetermined temperate.

23. A self-contained, single manual step unit for thermally sterilizing dental and medical instruments and other contaminated items according to claim 22 wherein said first temperature sensitive switch is a bimetal switch which is calibrated to automatically reset at 150° centigrade.

24. A self-contained, single manual step unit for thermally sterilizing dental and medical instruments and other contaminated items according to claim 1 wherein said electrical control system comprises a second temperature sensitive switch which is in caloric communication with said mater and which closes to end the sterilization cycle and begin a cooling cycle when said matter reaches a predetermined temperature.

25. A self-contained, single manual step unit for thermally sterilizing dental and medical instruments and other contaminated items according to claim 24 wherein said second temperatures sensitive switch is a bimetal switch which closes at 120° centigrade.

26. A unit for thermally sterilizing dental and medical instruments and other contaminated items comprising:
  an insulating and protective housing comprising an orifice for ingress and egress of items to be sterilized;
  a vessel disposed within said housing which comprises an inner contiguous vertical wall, which is closed at the bottom to form a medially disposed well wherein items are sterilized and cooled thereafter, and unobstructed at the top which provides an accessible opening through said orifice;

said unit further comprising a thermal regulation assembly disposed in caloric communication with sail vessel, said assembly comprising an inner wall and a juxtaposed outer wall separated therefrom and sealed thereto to form a chamber;

said thermal regulation assembly further comprising a cooling subassembly having a cooling coil disposed in caloric communication with said thermal regulation assembly inner wall; a predetermined quantity of matter, which change state at a predetermined temperature which is consistent with sterilizing, hermetically sealed within said chamber;

a disengageable lid which covers, protects and seals said accessible opening when engaged and which permits access to said well when disengaged;

at least one heater disposed in caloric communication with said matter, said heater having adequate thermal output to heat water to generate steam;

a container, placed within the well, containing the items to be sterilized;

a capsule of water disposed within the container, at least a portion of which is transformed to steam as part of the sterilization cycle, said capsule being perforated when water is heated during the sterilization cycle; and an electrical control system which limits duration of the sterilization cycle and temperature in the well to assure the container is not irreversibly damaged during the sterilization cycle.

27. A unit for thermally sterilizing dental and medical instruments and other contaminated items according to claim 26 wherein said electrical control system automatically initiates a cooling cycle at the end of the sterilization cycle.

28. A unit for thermally sterilizing dental and medical instruments and other contaminated items according to claim 26 wherein said capsule comprises a frustoconically shaped package having a lid which in combination encloses and keeps pure a quantity of water, a portion of which is released during the sterilization cycle to provide the steam.

29. A unit for thermally sterilizing dental and medical instruments and other contaminated items according to claim 26 wherein said container is a protective wrap disposed about the capsule and items to be sterilized.

30. A unit for thermally sterilizing dental and medical instruments and other contaminated items according to claim 26 wherein said container is a synthetic resinous material which withstands and maintains containment of the items contained therein throughout the sterilization cycle.

* * * * *